United States Patent
Csizmadia et al.

(10) Patent No.: US 9,243,031 B2
(45) Date of Patent: Jan. 26, 2016

(54) COMPLEX-FORMING COMPOUNDS

(71) Applicant: STRATOXER(S) KFT., Varpalota (HU)

(72) Inventors: G. Imre Csizmadia, Szeged (HU); Zoltan Mucsi, Budapest (HU); Andrea Narcisz Koczkas, Budapest (HU)

(73) Assignee: STRATOXER(S) KFT., Varpalota (HU)

( * ) Notice: Subject to any disclaimer, the term of this patent is extended or adjusted under 35 U.S.C. 154(b) by 0 days.

(21) Appl. No.: 14/369,868

(22) PCT Filed: Dec. 28, 2012

(86) PCT No.: PCT/HU2012/000145
§ 371 (c)(1),
(2) Date: Jun. 30, 2014

(87) PCT Pub. No.: WO2013/098572
PCT Pub. Date: Jul. 4, 2013

(65) Prior Publication Data
US 2014/0342997 A1 Nov. 20, 2014

(30) Foreign Application Priority Data
Dec. 30, 2011 (HU) .................. 1100731

(51) Int. Cl.
| | | |
|---|---|---|
| *C07D 273/08* | (2006.01) |
| *A61K 31/31* | (2006.01) |
| *A61K 31/32* | (2006.01) |
| *A61K 38/05* | (2006.01) |
| *C07K 5/078* | (2006.01) |

(52) U.S. Cl.
CPC ............ *C07K 5/06139* (2013.01); *A61K 31/31* (2013.01); *A61K 31/32* (2013.01); *C07D 273/08* (2013.01); *A61K 38/05* (2013.01)

(58) Field of Classification Search
CPC .. C07D 273/08; C07K 5/06139; A61K 38/05; A61K 31/32; A61K 31/31
See application file for complete search history.

(56) References Cited

FOREIGN PATENT DOCUMENTS

| | | |
|---|---|---|
| EP | 0369733 A2 | 5/1990 |
| HU | 209389 A | 5/1994 |
| WO | 9014343 A1 | 11/1990 |
| WO | 9110655 A1 | 7/1991 |

OTHER PUBLICATIONS

Staudinger, K. C., "Occupational lead poisoning." American family physician 57.4 (1998): 719-26.*
Goyer, R. A., "Chelation of toxic metals: current interests." Environmental health perspectives 103.11 (1995): 988-989.*
International Search Report for PCT/HU2012/000145 dated May 29, 2013.
Yost et al., "Crown ether-doped sol-gel materials for strontium(II) separation," Anal. Chem., 2000, vol. 72, pp. 5516-5519.
Brucher et al., "1, 10-Diaza-4, 7, 13, 16-tetraoxacyclooctadecane-1, 10-bis (malonate), a ligand with high Sr2+/Ca2+ and Pb2+/ Zn2+ selectivities in aqueous solution," J. Chem. Soc. Chem. Comm., 1993, vol. 6, pp. 574-575.

* cited by examiner

*Primary Examiner* — Samantha Shterengarts
*Assistant Examiner* — Matt Mauro
(74) *Attorney, Agent, or Firm* — Millen, White, Zelano & Branigan, P.C.

(57) ABSTRACT

Present invention refers to complex-forming compounds of the general formula

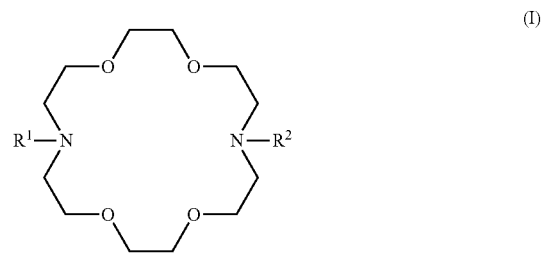

(I)

and the use and preparation thereof.

30 Claims, 7 Drawing Sheets

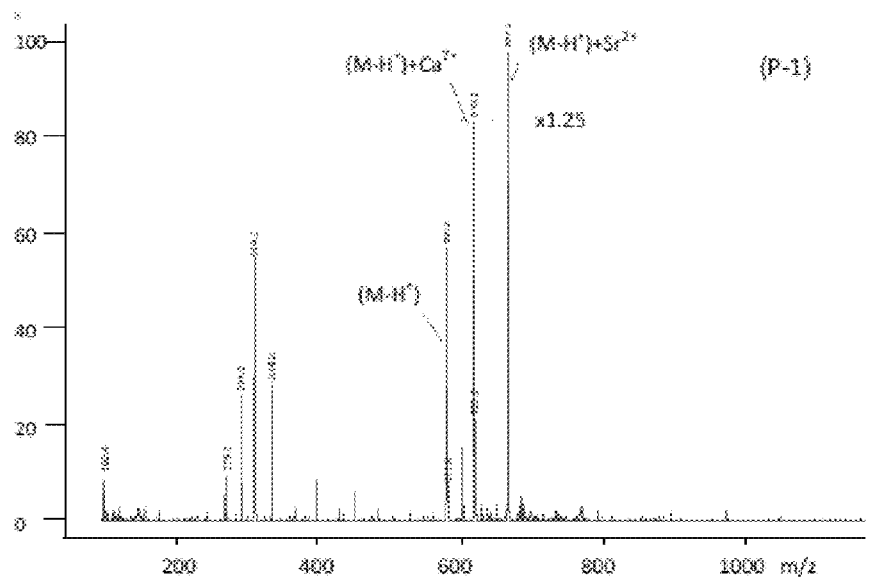
Fig 1-A
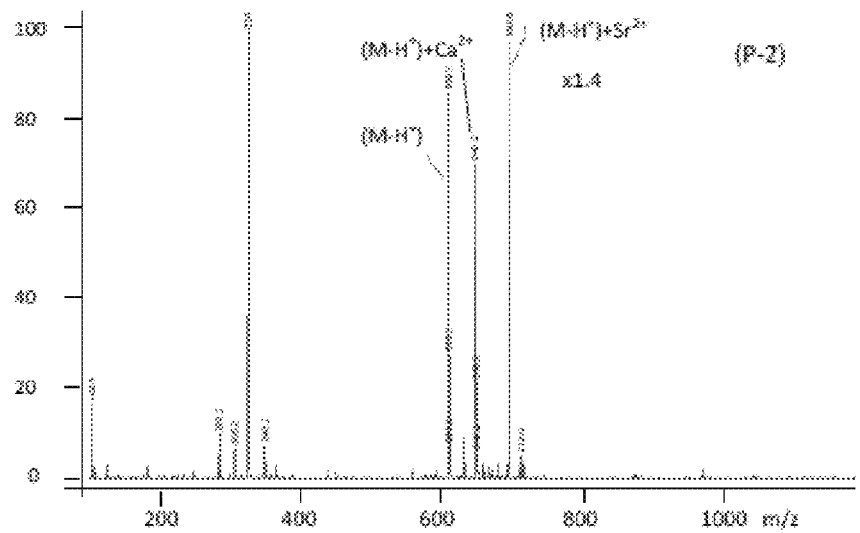
Fig 1-B

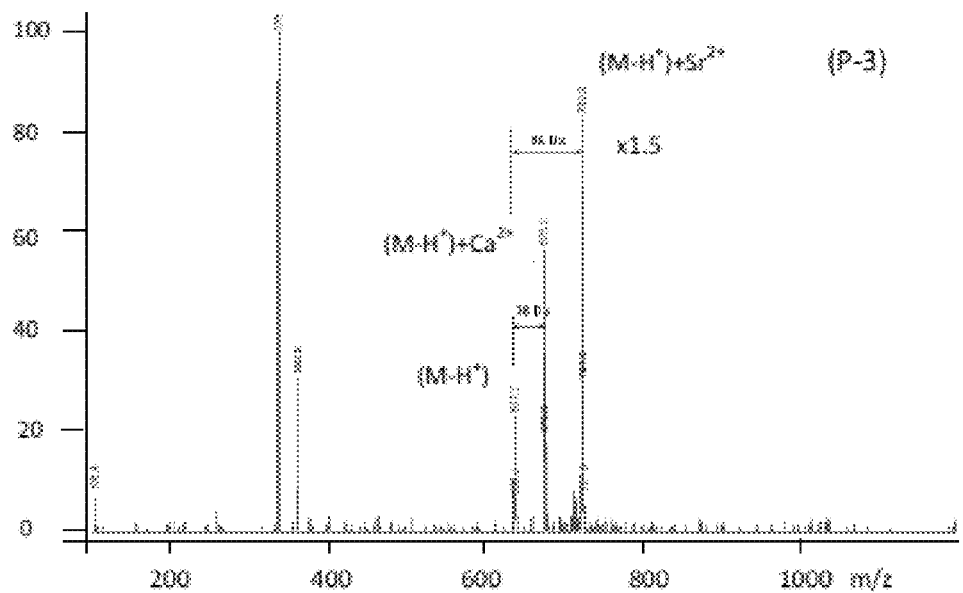
Fig 2-A
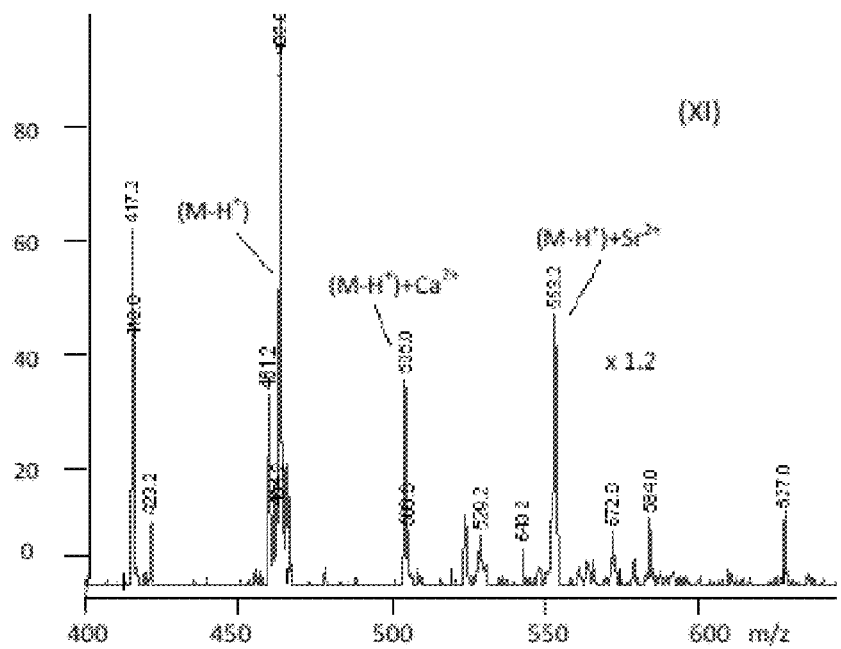
Fig 2-B

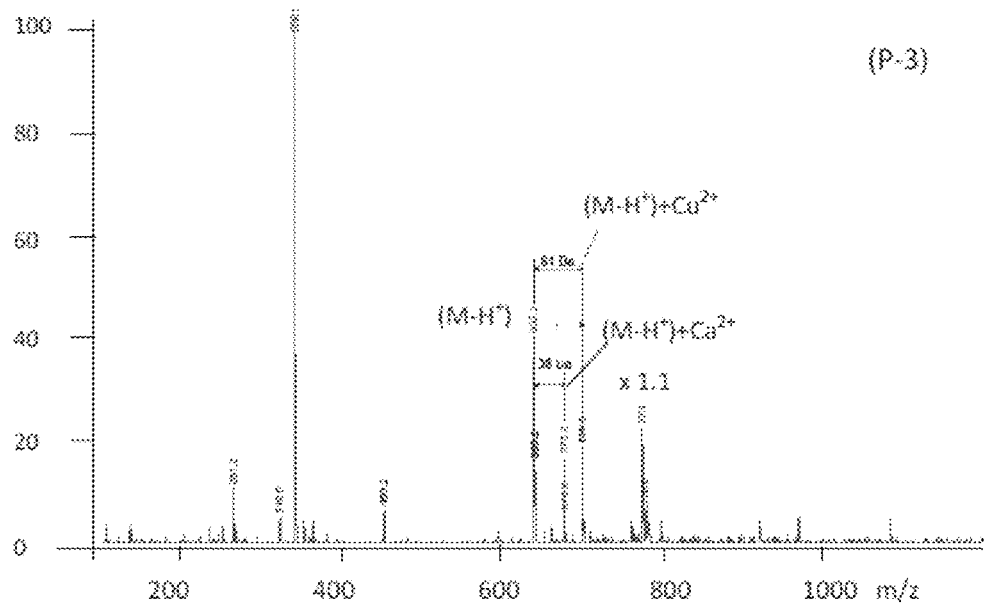
Fig 3-A
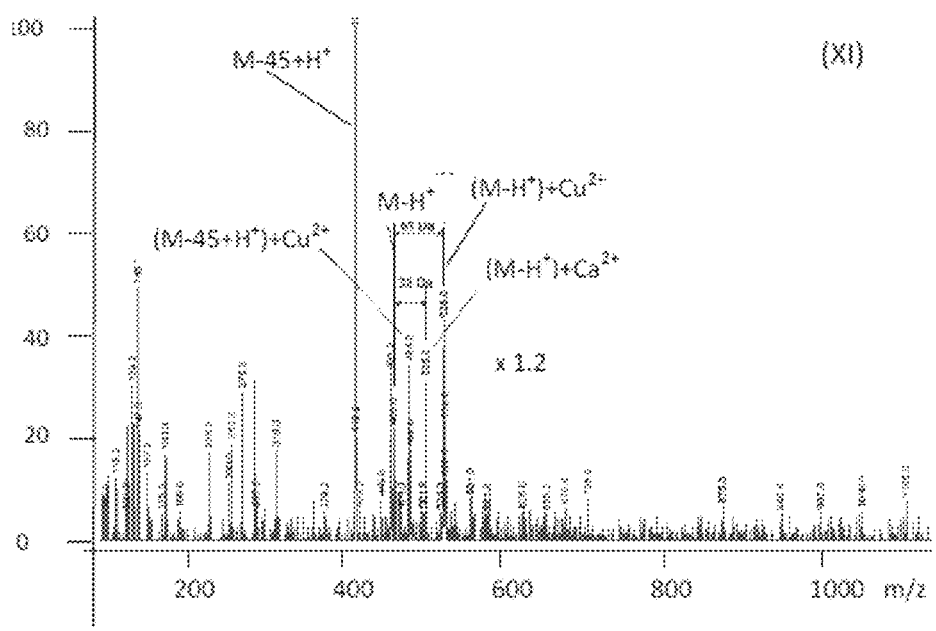
Fig 3-B

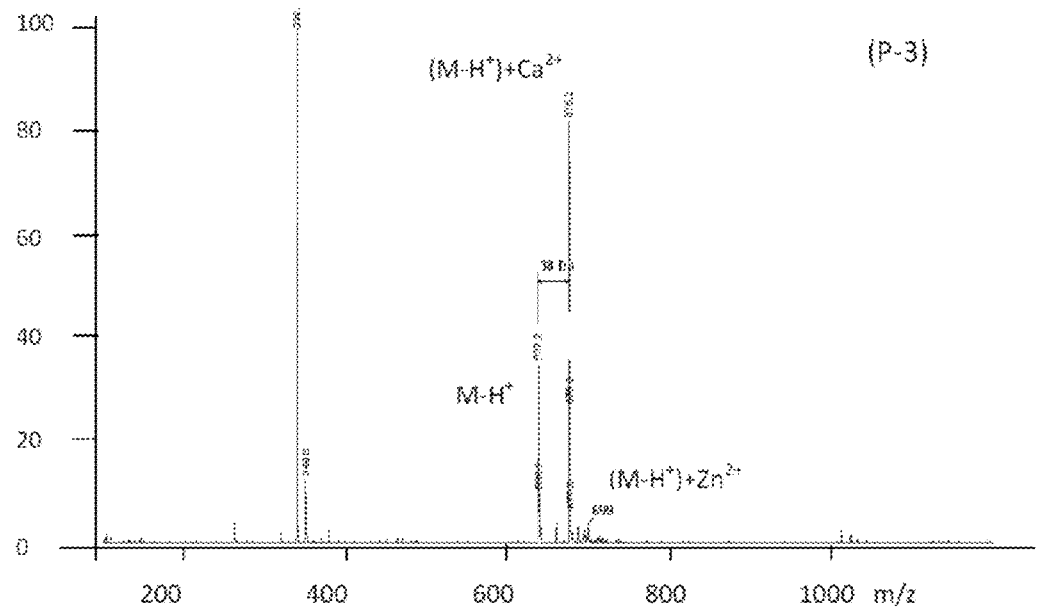
Fig 4-A
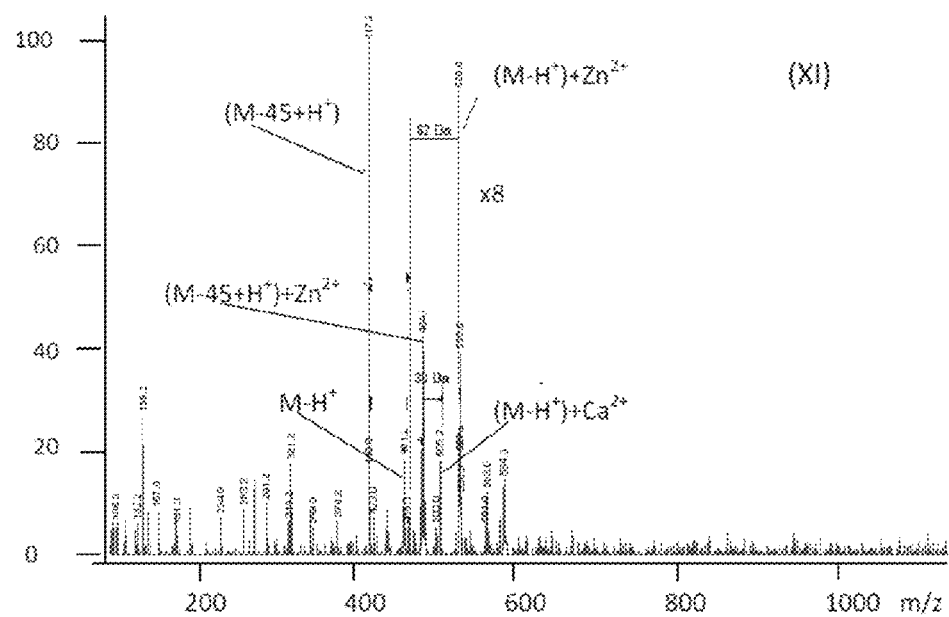
Fig 4-B

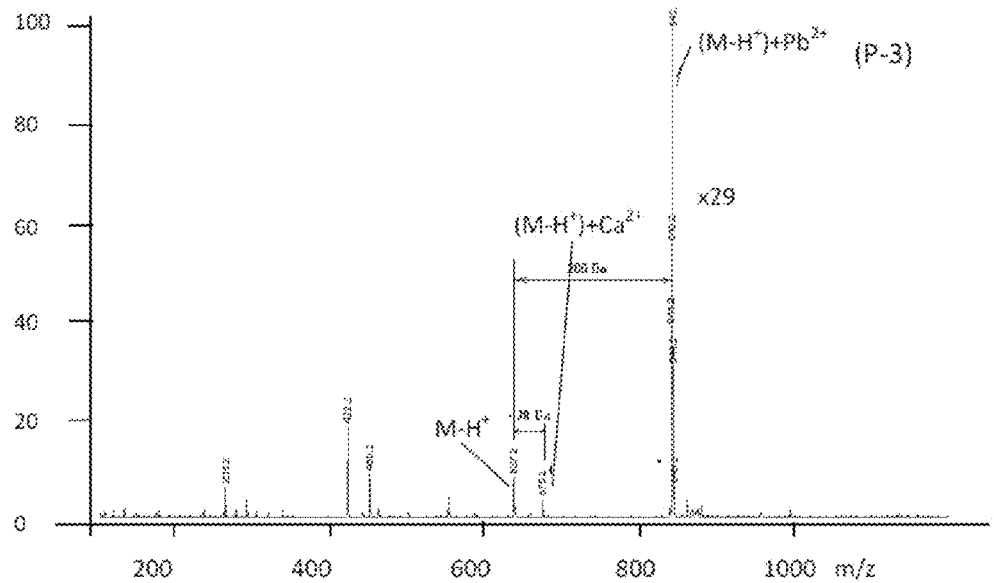
Fig 5-A
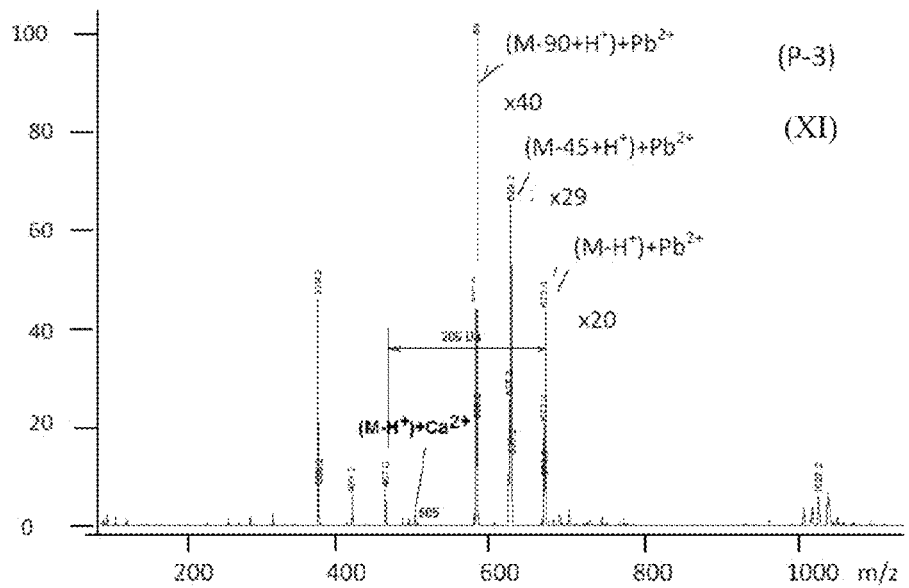
Fig 5-B

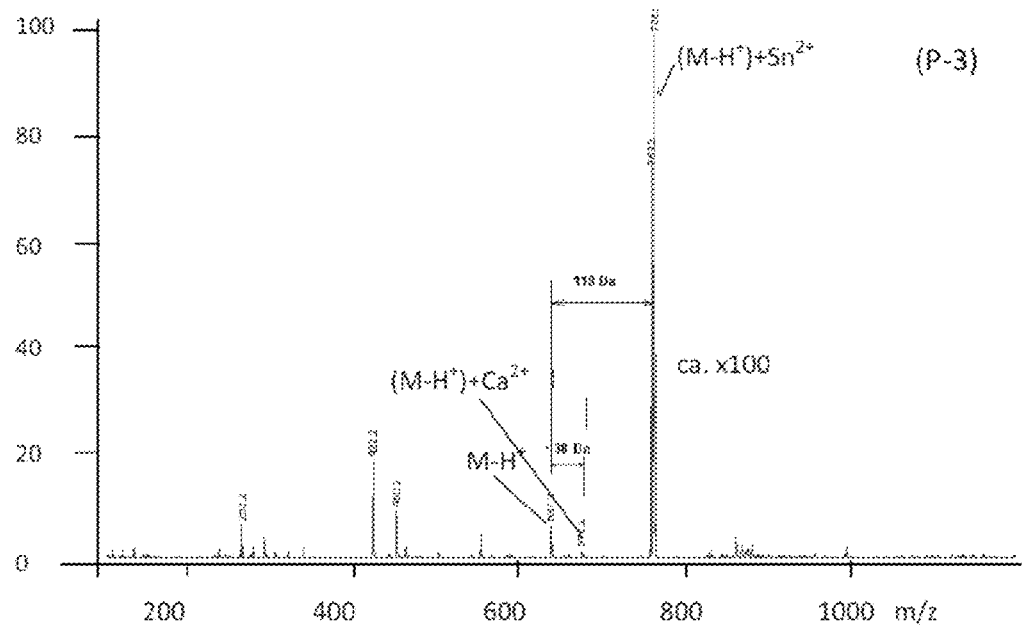
Fig 6-A
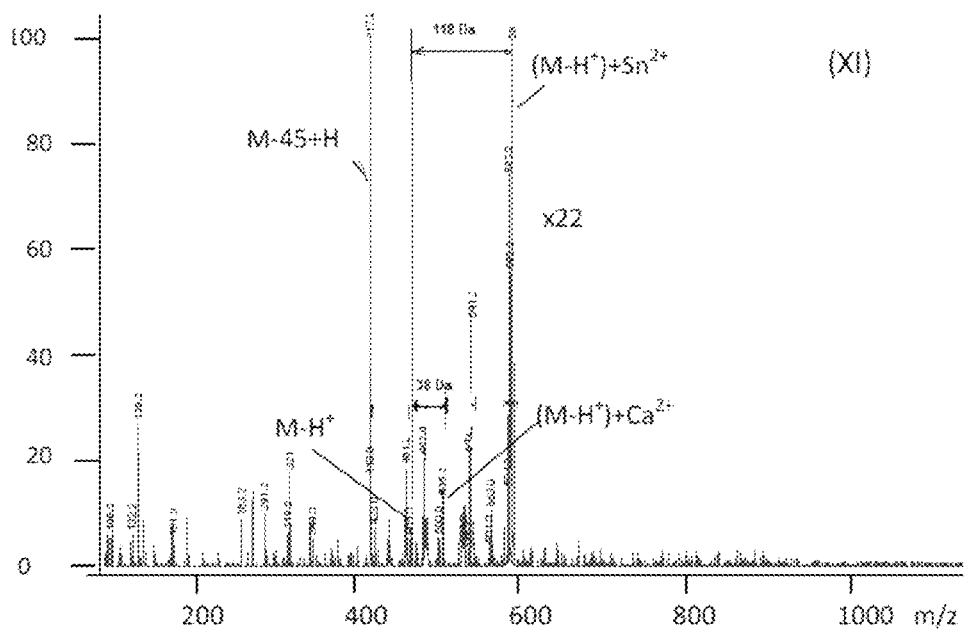
Fig 6-B

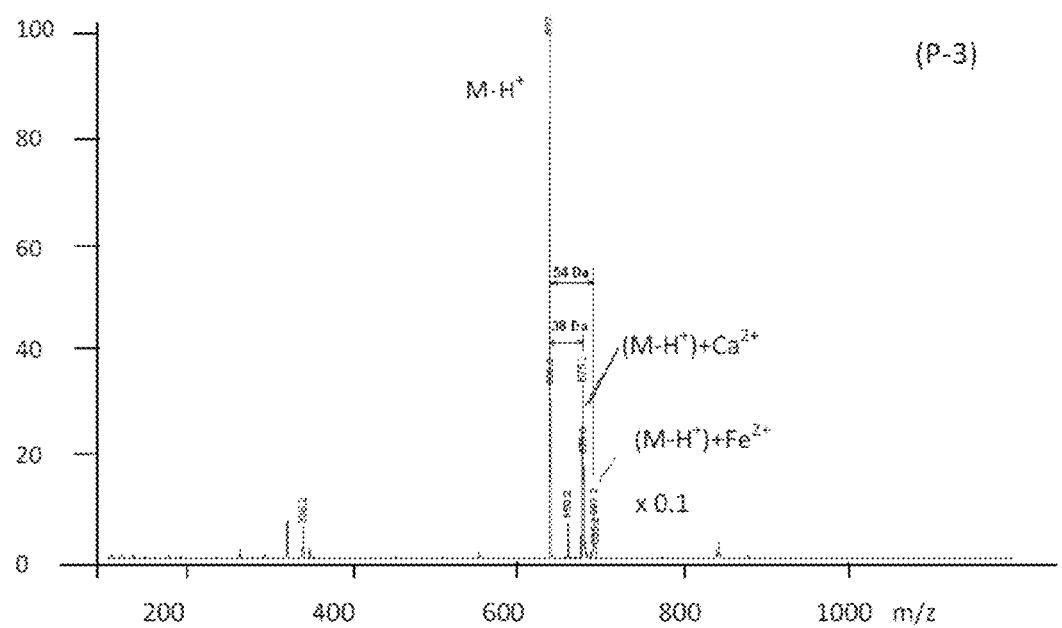
Fig 7-A

COMPLEX-FORMING COMPOUNDS

SUBJECT OF THE INVENTION

The present invention refers to the compounds of the general formula

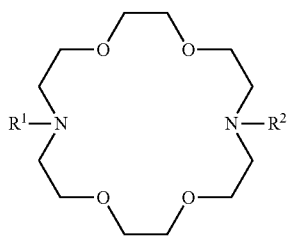

(I)

the preparation thereof and the use of these compounds for the prevention and treatment of heavy metal poisoning. Particularly, the present invention refers to a compound of the formula (I) which contains a structure of 1,4,10,13-tetraoxa-7,16-diazacylooctadekane (shortly KRIPTOFIX base structure) and in which each of the two nitrogen atoms are substituted with an identical or different group of the general formula

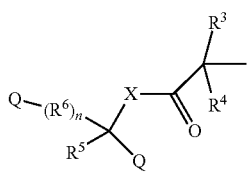

(II)

THE TECHNICAL BACKGROUND OF THE INVENTION

As a consequence of the environmental pollution due to the intensive industrialization and the consumption many poisonous compounds can accumulate in the human body and in the environment. From these compounds the most important ones are the lead (Pb) and the mercury (Hg) which can accumulate in the fatty tissue and cause severe acute or fatal poisoning. Radioactive strontium (Sr) and caesium (Cs) releasing to the environment as a consequence of nuclear catastrophes (Three-miles Island, N.Y. 1979; Chernobyl, USSR: 1986; Fukusima, Japan: 2011, Csillebérc, Hungary: 2011) and causing environmental, health and social damages accumulate in the bones and result in long-lasting poisoning.

For the removal of the above-mentioned poisoning compounds so called "chelate-forming" compounds can be used which remove the toxic metals from the body.

In the most cases these compounds have no specific effect. For example, in the case of ethylene-diamine-tetraacetic acid (EDTA) or diethylene-triamine-pentaacetic acid the calcium complexes are more stable than the strontium complexes, as described in lines 15-18 of the first paragraph on page 3 of the Hungarian Patent No. 209389. Since these complexes are not specific, during the use of them essential metals (such as Ca and Mg) can also be removed. Therefore in the Hungarian Patent No. 209386 more specific macrocyclic compounds, so called "criptand" derivatives were suggested for the removal of the strontium from the body. The parameters of the molecular structure of the macrocyclic compounds define which ion is bound to the compounds the strongest, thus for the specific removal of the different toxic metal ions complex-forming compounds are necessary, which bind the toxic metal ions significantly better.

The Hungarian Patent No. 209386 discloses such complex-forming agents which are based on a Kriptofix compound binding the strontium selectively. One member of these compounds is the compound of the formula

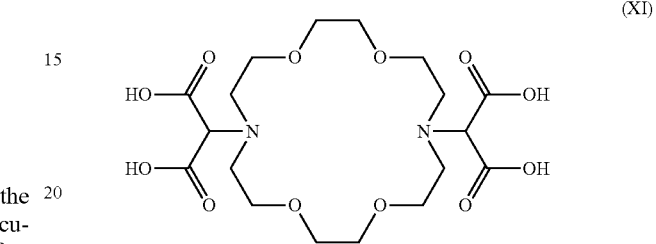

(XI)

(7,16-bis-malonate)-1,4,10,13-tetraoxa-7,16-diazacyclooctadecane-bis-malonic acid, which was prepared in Ca complex form as well. The compound of the formula (XI) verified a stronger activity with strontium than calcium in physico-chemical and in vivo experiments on mice. In the in vivo experiments the strontium administered artificially in a different amount could be removed selectively by the compound of the formula (XI) added intravenously, thus preventing its accumulation in the bones, while the calcium remained.

Furthermore, in vitro experiments show affinity with other toxic metal ions, which strengthens the usability of this compound. The efficacy of this compound is shown in examples 18 and 19 of the Hungarian Patent 209386. In these examples a salt of the compound of the formula (XI) is added intravenously into the body of rats in an amount of 50-100 micromoles/body weight kilogram. Taking into consideration that the molecular weight of the complexes and salts of the compound of the formula (XI) is 550-650, the single dose having an excellent effect for an adult human patient (70 body weight kg) can be even 4-4.5 g. According to the last line of the second column on page 3, and in lines 1-2 of the first column on page 4 of the description of the Hungarian Patent No. 209389 the salts of the compound of (XI) were administered intravenously in a concentration of 100-500 mg/l in animal experiments. A further disadvantage of the compound of the formula (XI) is that the malonic acid sub-structure decarboxylates easily and the strontium complex of the resulted compound is not soluble and precipitates from the aqueous medium, which can prevent the excretion of the strontium ion from the body. In course of another decomposition of the compound malonic acid cleaves from the compound which is a strong cytotoxin. The reason for this feature is that its structure is similar to that of the succinic acid which has a key role in the cellular respiration and therefore inhibits the function of succinate dehydrogenase enzyme. The tendency of decarboxylation can increase in the presence of other heavy metals having Lewis acidic properties such as lead (Pb) or tin (Sn), which is proved by our experimental results measured with mass spectrometer. The decarboxylation also reduces the complex-forming effect.

Therefore an idea has arisen to prepare complex-forming agents, the selectivity of which is similar to the compound of the formula (XI), but more effective, more water soluble, and do not transform to toxic compounds in course of their incidental metabolism in the body and are stable during storage. These compounds would allow the reduction of the amount of used dose. Since these compounds are usually used in catastrophes, they have to be stored in a large amount and for a long time.

The mere fact that compounds have 1.5-2 fold more effective complex-forming compounds than the known ones, reduces significantly the expenses of the preparation for catastrophes. On the other hand it is also important that the complex-forming compounds do not bind significantly and do not remove the microelements from the body which are important for the living beings such as zinc and copper.

THE ESSENCE OF THE INVENTION

The objects were achieved according to the present invention with the complex-forming compounds of the general formula (I) which contains a structure of 1,4,10,13-tetraoxa-7,16-diazacyclooctadekane (shortly KRIPTOFIX base structure) and in which each of the two nitrogen atoms is substituted with an identical or different group of the general formula (II). These compounds are suitable for the achievement of the above mentioned aims.

DETAILED DESCRIPTION OF THE INVENTION

The most general embodiment of the present invention is a compound of the general formula (I) in which $R^1$ and $R^2$ are identical or different groups according to the general formula

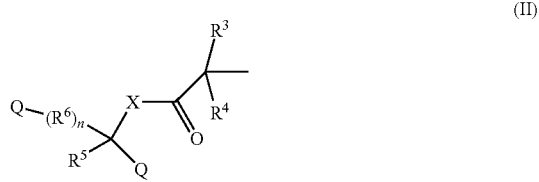

(II)

wherein n stands for 0, 1 or 2, Q is a carboxyl group, X stands for an oxygen, sulfur or a nitrogen atom, in which the substituent of the nitrogen atom is a hydrogen atom or a straight or branched $C_{1-6}$ carbon chained alkyl group, $R^3$, $R^4$ and $R^5$ are identical or different groups which stand for hydrogen, halogen atom, a straight or branched $C_{1-6}$ carbon chained alkyl group, $C_{1-6}$ alkylene group, $C_{1-6}$ alkynyl group, aryl, aralkyl or heteroaryl group, saturated or unsaturated cycloalkyl group, a substituted or unsubstituted heteroaryl group containing one or more sulfur, oxygen or nitrogen atoms, and which contains one or more identical or different substituents optionally which substituents are preferably $C_{1-6}$ alkyl group, halogen atom, a straight or branched $C_{1-6}$ carbon chained alkyl group, $C_{1-6}$ alkylene group, $C_{1-6}$ alkynyl group, aryl, aralkyl or heteroaryl group, saturated or unsaturated cycloalkyl group, a substituted or unsubstituted heteroaryl group, a substituted or unsubstituted heteroaryl group containing one or more sulfur, oxygen or nitrogen atoms, and which contains one or more identical or different substituents, hydroxyl group, alkoxy group, amino group, carboxyl group, alkoxycarbonyl group or carbamoil group, optionally $R^5$ and $R^6$ together form a double bond,
$R^6$ is a saturated or unsaturated $C_1$-$C_2$ alkyl group, which contains as substituents optionally one or more identical or different halogen atoms, a straight or branched $C_{1-6}$ carbon chained alkyl group, $C_{1-6}$ alkylene group, $C_{1-6}$ alkynyl group, aryl, aralkyl or heteroaryl group, saturated or unsaturated cycloalkyl group, a substituted or unsubstituted heteroaryl group containing one or more sulfur, oxygen or nitrogen atoms, which substituents optionally contain one or more further identical or different substituents, which are preferably halogen atom or a straight or branched $C_{1-6}$ carbon chained alkyl group, $C_{1-6}$ alkylene group, $C_{1-6}$ alkinyl group, aryl, aralkyl or heteroaryl group, saturated or unsaturated cycloalkyl group, a substituted or unsubstituted heterocyclic group containing one or more sulfur, oxygen or nitrogen atoms, hydroxy group, alkoxy group, carboxyl group, alkoxycarbonyl group, or carbamoil group and optionally $R^6$ is a group of the general formula

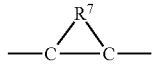

(III)

wherein the two carbon atoms and $R^7$ together stand for an unsubstituted or substituted 3-7 membered ring which is a saturated or unsaturated cycloalkyl ring or an isolated or condensed 3-7 membered saturated or unsaturated heterocyclic compound containing one or more heteroatoms, preferably sulfur oxygen or nitrogen, or an isolated or condensed aryl group or a heteroaryl group containing one or more sulfur, oxygen or nitrogen atoms in which as a substituents of the group of the formula (III) are one or more different substituents, preferably halogen atoms, hydroxyl group, alkoxy group, amino group, carboxyl group, alkoxycarbonyl group, carbamoyl group, and optionally $R^5$ and $R^6$ together stand for an unsubstituted or substituted 3-7 membered ring which is a saturated or unsaturated cycloalkyl ring or an isolated or condensed 3-7 membered saturated or unsaturated heterocyclic compound containing one or more heteroatoms, preferably sulfur, oxygen or nitrogen which contains as a substituent of the cyclic group one or more halogen atoms, hydroxyl group, $C_{1-6}$ alkyl group, $C_{1-6}$ alkylene group, $C_{1-6}$ alkinyl group, alkoxy group, amino group, carboxyl group, alkoxycarbonyl group or carbamoyl group and salts and/or complexes thereof.

According to the embodiments of the present invention wherein $R^1$ and $R^2$ are different, n, X, $R^3$, $R^4$, $R^5$, $R^6$ and $R^6$ can be partly identical or totally different in the two groups. In this case the compound is asymmetric.

According to the embodiments of the present invention wherein $R^1$ and $R^2$ are identical, n, X, $R^3$, $R^4$, $R^5$, $R^6$ and $R^6$ are identical thus the compound is symmetric.

We found that the compounds according to the present invention are highly selective and effective in the binding of strontium ion as well as the tin and lead ions.

Since there is no appropriate analytical method for the measurement of the complex-forming properties of these compounds with sufficient accuracy, we determined the complex-forming constants compared to the calcium ion complexes with high level quantum chemical calculations. The calculations were performed using Gaussian09 software on B3LYP/LANL2DZ theoretical level. In course of the calculations frequency calculations were also performed from which thermodynamic data were also determined.

According to the results shown in Tables 1-3 the compounds of the present invention bind strontium ion significantly more selectively than the compound of formula (XI). The ion binding capabilities to each of ions are compared to the calcium binding capabilities, which is shown by $R_H$ (relative complex-forming tendency).

TABLE 1

Calculated thermodynamic values of the $Ca^{2+}$ ion changing process of the compound of (XI) (kJ $mol^{-1}$).

| M | ΔE' | ΔH' | ΔG' | $R_H$ |
|---|---|---|---|---|
| $Mg^{2+}$ | 150.70 | 146.47 | 121.64 | $\sim 10^{-24}$ |
| $Ca^{2+}$ | 0.00 | 0.00 | 0.00 | 1.00 |
| $Sr^{2+}$ | −2.75 | −4.40 | −3.23 | 5.00 |
| $Ba^{2+}$ | −0.22 | −3.66 | 1.18 | 4.33 |

TABLE 2

Calculated thermodynamic values of the $Ca^{2+}$ ion changing process of the compound of the formula (P-1) (kJ $mol^{-1}$).

| M | ΔE' | ΔH' | ΔG' | $R_H$ |
|---|---|---|---|---|
| $Mg^{2+}$ | 33.50 | 33.61 | 19.05 | $1*10^{-6}$ |
| $Ca^{2+}$ | 0.00 | 0.00 | 0.00 | 1.00 |
| $Sr^{2+}$ | −7.53 | −7.88 | −5.87 | 20.87 |
| $Ba^{2+}$ | −1.38 | −2.65 | −1.84 | 2.90 |

TABLE 3

Calculated thermodynamic values of the $Ca^{2+}$ ion changing process of the of the macrocycle compound of the formula (P-2) (kJ $mol^{-1}$).

| M | ΔE' | ΔH' | ΔG' | $R_H$ |
|---|---|---|---|---|
| $Mg^{2+}$ | 37.49 | 37.06 | 21.91 | $3*10^{-6}$ |
| $Ca^{2+}$ | 0.00 | 0.00 | 0.00 | 1.00 |
| $Sr^{2+}$ | −6.56 | −7.49 | −4.81 | 18.26 |
| $Ba^{2+}$ | 0.38 | −0.61 | 1.84 | 1.28 |

The strontium binding affinity of the compounds of formulae

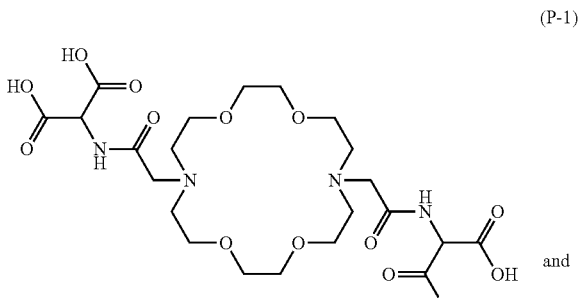

(P-1)

and

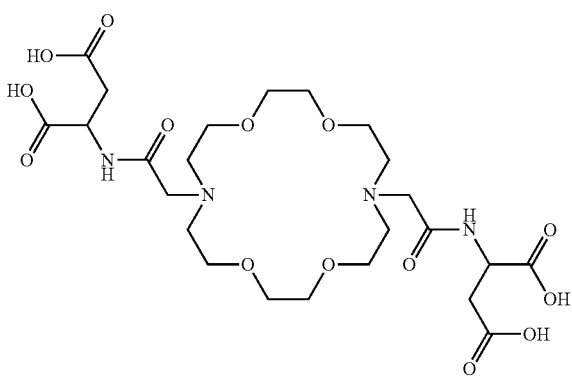

(P-2)

according to the present invention in case of (P-1) is more than 4 fold ($R_H$=20.87), in case of (P-2) approximately 4 fold ($R_H$=18.26) compared to the compound of the affinity of formula (XI) ($R_H$=5.00).

That means that using the compounds of the present invention the quantity of the active ingredient to be stored will be one fourth of the quantity to be stored in other cases and the load exerted on the organism during the treatment reduces at the same extent, while the same therapeutic effect can be achieved. Furthermore, in case of the incidental decomposition of the compounds of the preferable embodiments of the present invention the degradation products are amino- or hydroxy acids which are not harmful for the body.

The thermodynamic data (ΔE, ΔH, ΔG) were calculated with mathematical equations from the values of E, H and G counted on quantum chemical basis:

$$\Delta E[complex-M] = E[complex-M] + E[CaCl_2 \cdot 6H_2O] - \{E[complex-Ca] + E[MCl_2 \cdot 6H_2O]\}$$

$$\Delta H[complex-M] = H[complex-M] + H[CaCl_2 \cdot 6H_2O] - \{H[complex-Ca] + H[MCl_2 \cdot 6H_2O]\}$$

$$\Delta G[complex-M] = G[complex-M] + G[CaCl_2 \cdot 6H_2O] - \{G[complex-Ca] + G[MCl_2 \cdot 6H_2O]\}$$

The relative complex-forming constant ($R_G$) compared to the $Ca^{2+}$ ion can be calculated with the following equation:

$$R_G = \frac{K_{M^{2+}}}{K_{Ca^{2+}}} = \exp\left(\frac{-\Delta G}{RT}\right)$$

Since the quotient formation expectedly causes a loss of entropy coefficients, the following equation was used which is more practical due to the fluctuation of the calculated entropy coefficient:

$$R_H = \exp\left(\frac{-\Delta H}{RT}\right)$$

According to a more advantageous embodiment of the present invention there are the compounds provided of the general formula (I), wherein the substituents of $R^1$ and $R^2$ are identical or different groups of the general formula (II), wherein n stands for 0, 1 or 2, X stands for an oxygen atom or an unsubstituted or substituted nitrogen atom and the substituent of the nitrogen atom is a hydrogen atom or a methyl group, the meaning of the substituents $R^3$, $R^4$, $R^5$, $R^6$ are as mentioned above and the salts and/or complexes thereof.

According to a further embodiment of the present invention there are the compounds provided of the general formula (I), wherein the substituents of $R^1$ and $R^2$ are identical or different groups of the general formula (II), wherein n stands for 0, 1 or 2, Q stands for a carboxyl group, X stands for an oxygen atom or an unsubstituted or substituted nitrogen atom and the substituent of the nitrogen atom is a hydrogen atom or a methyl group, the meaning of the substituents $R^3$, $R^4$, $R^5$, $R^6$ are as mentioned above and the salts and/or complexes thereof.

According to a further advantageous embodiment of the present invention there are the compounds provided of the general formula (I) and the salts and/or complexes thereof, wherein the substituents of $R^1$ and $R^2$ are identical or different groups of the general formula (II), wherein n stands for 0, 1 or 2, Q stands for a carboxyl group, X stands for an oxygen atom or an unsubstituted or substituted nitrogen atom and the substituent of the nitrogen atom is a hydrogen atom or a methyl group, the substituents $R^3$, $R^4$, $R^5$ are identical or different groups which stand for hydrogen atom, halogen atom, straight or branched $C_{1-6}$ alkyl group, aryl or aralkyl group, $R^6$ stands for an unsubstituted or substituted methylene group which can be substituted with one or more identical or different substituents, halogen atoms, a straight or branched $C_{1-6}$ carbon chained alkyl group, $C_{1-6}$ alkylene group, $C_{1-6}$ alkinyl group, aryl, aralkyl or heteroaryl group, saturated or unsaturated cycloalkyl group, a substituted or unsubstituted heteroaryl group containing one or more sulfur, oxygen or nitrogen atoms, optionally $R^5$ and one substituent of $R^6$ together form an unsubstituted or a substituted 3-7 membered ring.

According to a more advantageous embodiment of the present invention the substituents of $R^1$ and $R^2$ of the general formula (I) are identical, in the groups of the general formula (II) n stands for 0, 1 or 2, Q stands for a carboxyl group, X stands for an unsubstituted or substituted nitrogen atom wherein the substituent of the nitrogen atom is a hydrogen atom or a methyl group, $R^3$, $R^4$, $R^5$ are identical or different, which stand for hydrogen atom, halogen atom, straight or branched $C_{1-6}$ alkyl group, aryl or aralkyl group, $R^6$ stands for an unsubstituted or substituted methylene group which can be substituted with one or more identical or different substituents, halogen atoms, or a straight or branched $C_{1-6}$ carbon chained alkyl group, $C_{1-6}$ alkylene group, $C_{1-6}$ alkinyl group, aryl, aralkyl or heteroaryl group, saturated or unsaturated cycloalkyl group, a substituted or unsubstituted heterocyclic group containing one or more sulfur, oxygen or nitrogen atoms, optionally $R^5$ and one substituent of $R^6$ together form an unsubstituted or a substituted 3-7 membered ring or in the most advantageous case $R^6$ stands for an unsubstituted or substituted methylene group which can be substituted with one or more identical or different substituents, straight or branched $C_{1-6}$ carbon chained alkyl group, $C_{1-6}$ alkylene group, $C_{1-6}$ alkinyl group.

The most advantageous embodiments of the present invention are the compounds 2-(2-{16-[(Dicarboxymethyl-carbamoyl)-methyl]-1,4,10,13-tetraoxa-7,16-diaza-cyclooctadec-7-yl}-acetiyamino)-malonic acid; 2-(2-{16-[(1,2-dicarboxy-ethylcarbamoyl)-methyl]-1,4,10,13-tetraoxa-7,16-diaza-cyclooctadec-7-yl}-acetylamino)-succinic acid; and 2-(2-{16-[(1,3-dicarboxy-propylcarbamoyl)-methyl]-1,4,10,13-tetraoxa-7,16-diaza-cyclolooctadec-7-yl}-acetylamino)-glutaric acid of the formula:

(P-3)

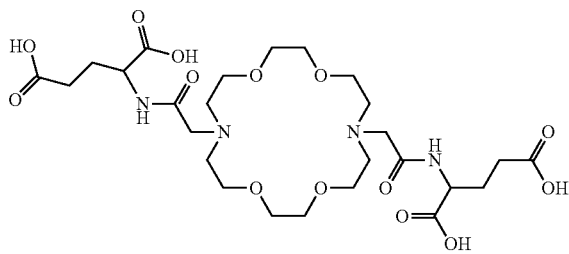

or salts or complexes thereof.

The complexes according to the present invention are preferably the complexes of calcium, magnesium, strontium, mercury and lead ions of the compounds of the general formula (I). The compounds according to the present invention have acid carboxyl groups and basic amino groups, thus they form salts with ammonia, amines and also with organic or inorganic acids. Further objects of the present invention are complex compounds being also salts formed with acids or with bases, for example such strontium complexes, in which the carboxyl groups are in a sodium salt form or such complexes in which the nitrogen atom forms a salt with an organic or inorganic acid. The salts composed either with acids or bases are more stable, can be better handled and are less hygroscopic than the compounds not stabilized with salt formation.

The organic acid components of the acid addition salts of the compounds of the formula (I) are preferably saturated or unsaturated, substituted or unsubstituted aliphatic carboxylic acids, e.g. formic acid, acetic acid, propionic acid, butyric acid, isobutyric acid, stearic acid, decanoic acid, sebacic acid, orotic acid, palmitic acid, pamoic acid, substituted carboxylic acids as carboxylic acids substituted with halogen atoms, e.g. chloroacetic acid, dichloroacetic acid, trifluoroacetic acid, or oxo acids such as 2-oxo-glutaric acid, pyruvic acid, di- and polycarboxylic acids such as oxalic acid, adipic acid, succinic acid, fumaric acid, maleic acid, malonic acid, aromatic carboxylic acids such as benzoic acid, salicylic acid, acetyl salicylic acid, 4-aminosalicylic acid, aliphatic or aromatic sulfonic acids such as methane-, ethanesulfonic acid, hydroxyethanesulfonic acid, cyclohexyl-sulfonic acid (cyclamic acid), dodecylsulphonic acid, ethane-1,2-disulfonic acid, p-toluenesulfonic acid, naphthalenesulfonic acid, naphthalene-2-sulfonic acid, naphthalene-1,5-disulfonic acid, carbohydrates with carboxyl functionality such as glucoheptoinoic acid, D-gluconic acid, D-glukuronic acid, hydroxy acids, such as ascorbic acid, (+)-L-lactic acid, (±)-DL-lactic acid, malic acid, amino acids such as L-aspartic acid, preferably an unsubstituted $C_1$-$C_4$ carboxylic acid or a carboxylic acid substituted with halogen atoms such as acetic acid, dichloroacetic acid, difluoroacetic acid, most preferably trifluoroacetic acid. As inorganic salt forming compounds, e.g. nitric acid, sulfuric acid, hydrogen bromide, phosphoric acid are used in a salt or in an acidic form.

In the description of the present invention the meaning of terms is as follows: straight or branched carbon chained $C_{1-6}$ alkyl groups are e.g. methyl, ethyl, propyl, isopropyl, butyl, tert-butyl, hexyl groups, $C_{1-6}$ alkylene groups are groups having one or more isolated or conjugated double bonds, e.g. 2-propenyl, isobutenyl groups, $C_{1-6}$ alkinyl groups are groups having one or more isolated or conjugated double bonds, or triple bonds e.g. propargyl groups. Aryl groups are substituted or unsubstituted, isolated or condensed isocyclic aromatic compounds such as phenyl and naphtyl groups. Aralkyl groups are such isocyclic groups which are connected to the structure through an alkylene, e.g. a methylene group. Heteroaryl groups are such compounds which contain at least one hetero atom such as pyridyl, pyrazonyl, imidazolyl, pyrazolyl, oxazolyl, thiophenyl groups or condensed heteroaryl groups such as purinyl groups. Saturated or unsaturated cycloalkyl groups are such groups as cyclopropyl, cyclobutyl, cyclohexyl, cycloheptyl or the derivatives thereof containing at least one double bond. Substituted or unsubstituted heterocyclic compounds are groups derived from cyclic compounds having at least one sulphur, oxygen or nitrogen ring member such as azetidinyl, oxyranyl, dioxolanyl, morpholinyl groups. Alkoxy groups are groups in which the alkyl group is attached to a carbon atom of the compound through an oxygen atom. The amino groups can be primary, secondary or tertiary amino groups according to the present invention. The alkoxycarbonyl groups are such esters in which the alcohol component is an alkyl or aralkyl group, such groups are e.g. ethoxy carbonyl, methoxycarbonyl or benzyloxicarbonyl groups. The carbamoyl groups can have one or two substituents. Halogen atoms are chloro, bromo, iodo or fluoro atom. Carbon containing acid is the carboxylic acid.

Another aspect of the present invention is the preparation of the compounds of the general formula (I) in which $R^1$ and $R^2$ are as defined above with synthesizes as follows:

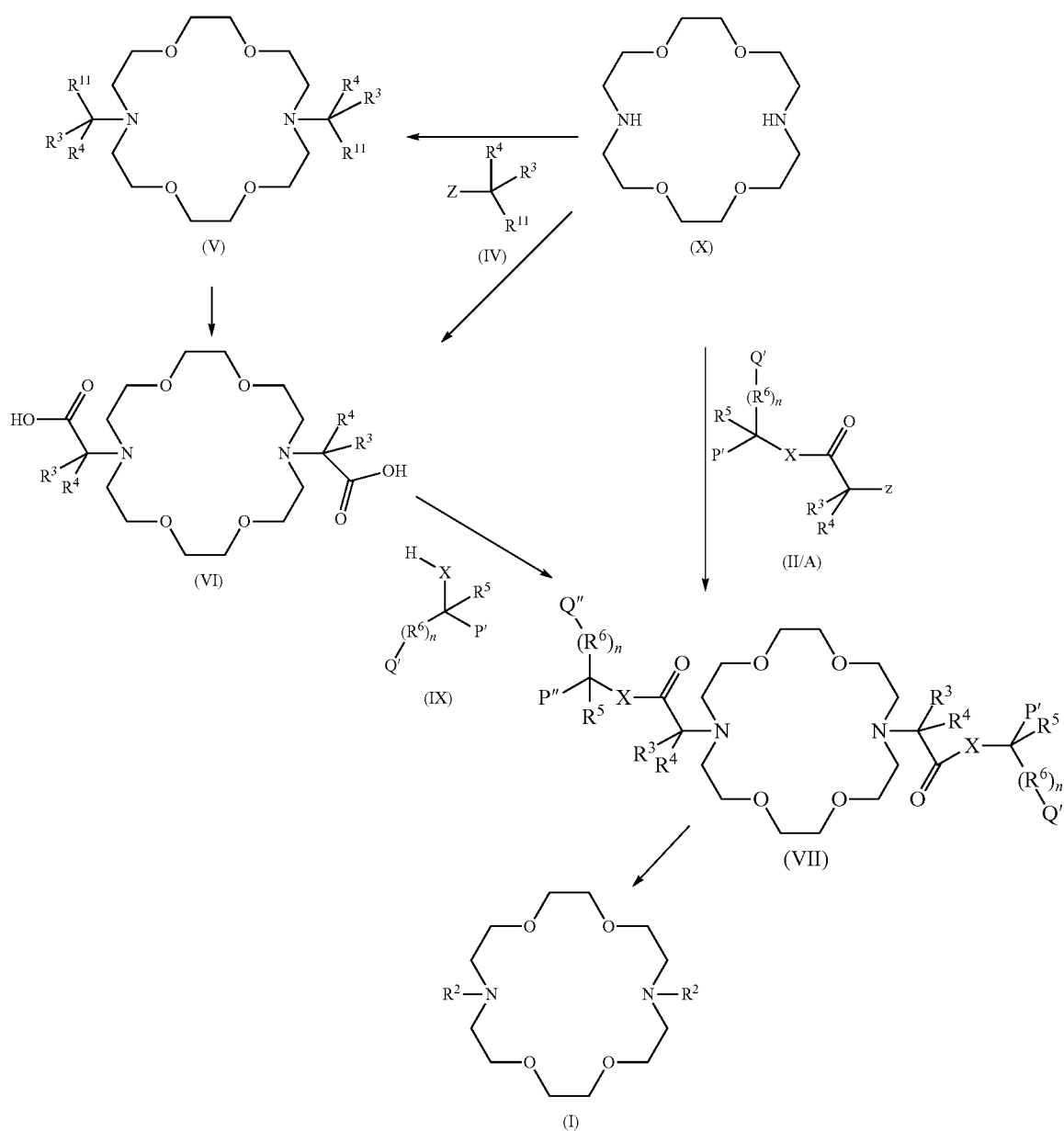

Another aspect of the present invention is the preparation of the compounds of the general formula (I), in which $R^1$ and $R^2$ are as defined above, characterized in that the compound of the formula (X) is reacted with a compound of the general formula of (II/A), in which the meaning of $R^3$, $R^4$, $R^5$, $R^6$, n and X is as defined above for group (II) and in which Q' and P' stand for carboxyl groups, Z is a leaving group, preferably a halogen atom, e.g. bromo, iodo, or chloro atom, or an aliphatic or aromatic sulfonyloxy group, such as a tosiloxy or mesyloxy group, or the P', P'', Q' and Q'' groups of the compound of the general formula (VII) are transformed carboxyl groups, wherein the meaning of $R^3$, $R^4$, $R^5$, $R^6$, n and X of the general formula (VII) is as defined above for group (II) and the P', P'', Q' and Q'' groups are identical or different protected carboxyl groups such as esters, amide or cyano groups, or the compound of the formula (VI), in which the meaning of $R^3$, $R^4$ is as defined above for group (II), is reacted with a compound of the general formula (IX), in which P' and Q' groups are carboxyl groups, or the compound of the formula (VI), in which the meaning of $R^3$, $R^4$ is as defined above for group (II), is reacted with a compound of the general formula (IX), in which P' and Q' groups are identical or different protected carboxyl groups such as esters, amides P' and/or Q' are cyano groups, then the carboxyl groups are deprotected from the resulted compound of the general formula (VII), then the thus obtained compound of general formula (I) is transformed into complex and/or salt form if necessary.

More specifically, one may proceed as follows:

a.)

The compound of the formula (X) is reacted with a compound of the general formula (II/A), in which the meaning of $R^3$, $R^4$, $R^5$, $R^6$, n and X is as defined above for group (II), P' and Q' groups are protected carboxyl groups such as esters, amide or P' and/or Q' are cyano groups, Z is a leaving group, preferably a halogen atom, e.g. bromo, iodo, or chloro atom, or an aliphatic or aromatic sulfonyloxy group, such as a tosyloxy or mesyloxy group. Then the protecting groups of the carboxyl groups of the obtained compound of the general formula (VII) are removed and the compound of the general formula (I) is obtained, or b.)

The compound of the formula (X) is reacted with a compound of the general formula (II/A), in which Q' and P' stand for carboxyl groups, and thus the compound of the general formula (I) is obtained.

Alternatively we can proceed that the compound of the formula (X) is reacted with a compound of the general formula (IV) in which the meaning of $R^3$ and $R^4$ is defined above, Z is a leaving group, preferably a halogen atom, e.g. bromo, iodo or chloro atom, or an aliphatic or aromatic sulfonyloxy group, such as a tosyloxy, benzenesulfonyloxy or mesyloxy group. $R^{11}$ group is a protected carboxyl group such as ester, amide or cyano group. The $R^{11}$ groups of the thus obtained compound of the general formula (V) are transformed to carboxyl groups. The obtained compound of the formula (VI) is reacted with a compound of the general formula (IX) wherein $R^5$, $R^6$ and X are as defined above, P' and Q' groups are protected carboxyl groups such as esters, amides or P' and/or Q' are cyano groups. Then the protecting groups of the obtained compound of the general formula (VII) are removed and the compound of the general formula (I) is obtained.

Alternatively, we can react the compound of the formula (X) with a compound of the general formula (IV) wherein $R^3$, $R^4$ and Z are as defined above, $R^{11}$ stands for a carboxyl group. In this case we obtain the compound of the formula (VI) in on step.

In the case the compound of the formula is reacted with a compound of the general formula (IX), wherein Q' and P' are carboxyl groups, the product of the reaction is the compound of the general formula (I).

The obtained compound of the general formula (I) can be transformed into a salt and/or complex if necessary.

In the case of the preparation of the compounds of the general formula (I) having an asymmetric structure we can also proceed that the compound of the formula (I), wherein both $R^1$ and $R^2$ are hydrogen atoms, is reacted with 0.5-1.5 mol equivalents of the compound of the general formula (II/A), wherein the meaning of $R^3$, $R^4$, $R^5$, $R^6$, $R^7$, Q, n and X is the same as defined above for the group of the general formula (II), Y is a leaving group, preferably bromo, iodo, or chloro atom, or an active ester, e.g. a sulfonyloxy group, preferably mesyloxy, tosyloxy, or benzenesulfonyloxy group, then preferably reacted with further 0.5-1.5 mol equivalents of a compound of the general formula (II/A) different from the other compound used in the first step, the obtained compound of the general formula (I), wherein the meaning of $R^1$ and $R^2$ is defined above, is isolated from the reaction mixture, purified if necessary and optionally transformed into a salt and/or complex form.

The reaction can be carried out in such a manner that the carboxyl groups of the compound of the formula (II/A) are applied first before the reaction with protecting groups which groups are removed after the reaction.

The reaction can be carried out in the presence of organic or inorganic bases, preferably in the presence of potassium or sodium carbonate or triethylamine.

The X group of the compound of the general formula (II/A) can stand for a sulphur, oxygen or nitrogen atom as defined above. From the point of view of the N-alkylation reaction there can be any of them because they do not take part in the reaction.

The compounds of the general formula (II/A) can be prepared in an analogous manner, namely an amino, hydroxyl or mercapto dicarboxylic acid or derivatives thereof with protected carboxyl functions are reacted with an unsubstituted or substituted chloro, bromo or iodo acetic acid halogenid, preferably with a chloride in the presence of a base in an indifferent solvent and the temperature of the reaction mixture is kept between –20-100° C., preferably between 40-80° C. The acylation of amino, mercapto and hydroxyl acids is well-known from the prior art, it is a part of the knowledge of the person skilled in the art.

The carboxyl groups are generally protected in ester form, preferably alkyl esters, e.g. tert. butyl esters or benzyl esters are used. The alkyl ester groups can be removed by hydrolysis, benzylesters by hydrogenation. These processes are well known from the prior art and are a part of the knowledge of the person skilled in the art, as the hydrolysis of other protecting groups, such as the transformation of amide group, cyano groups, and the orthoesters to carboxyl groups.

In the experimental part we show particularly the three different routes of synthesis of the general formula (I), in which the acid groups are carboxyl groups as follows:

Route of Synthesis A:

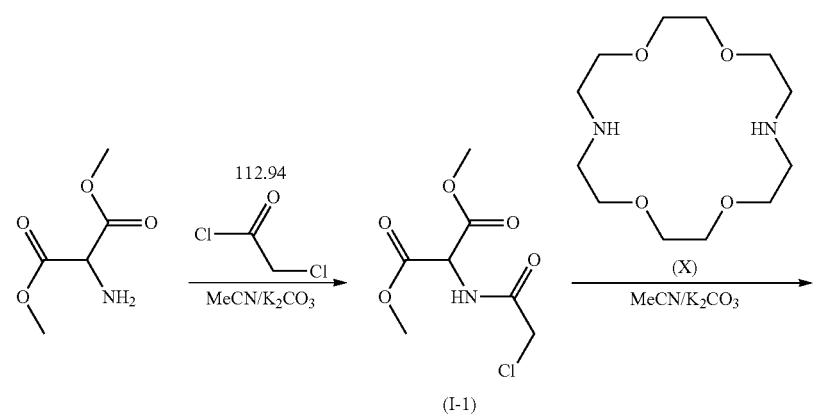

(I-1)

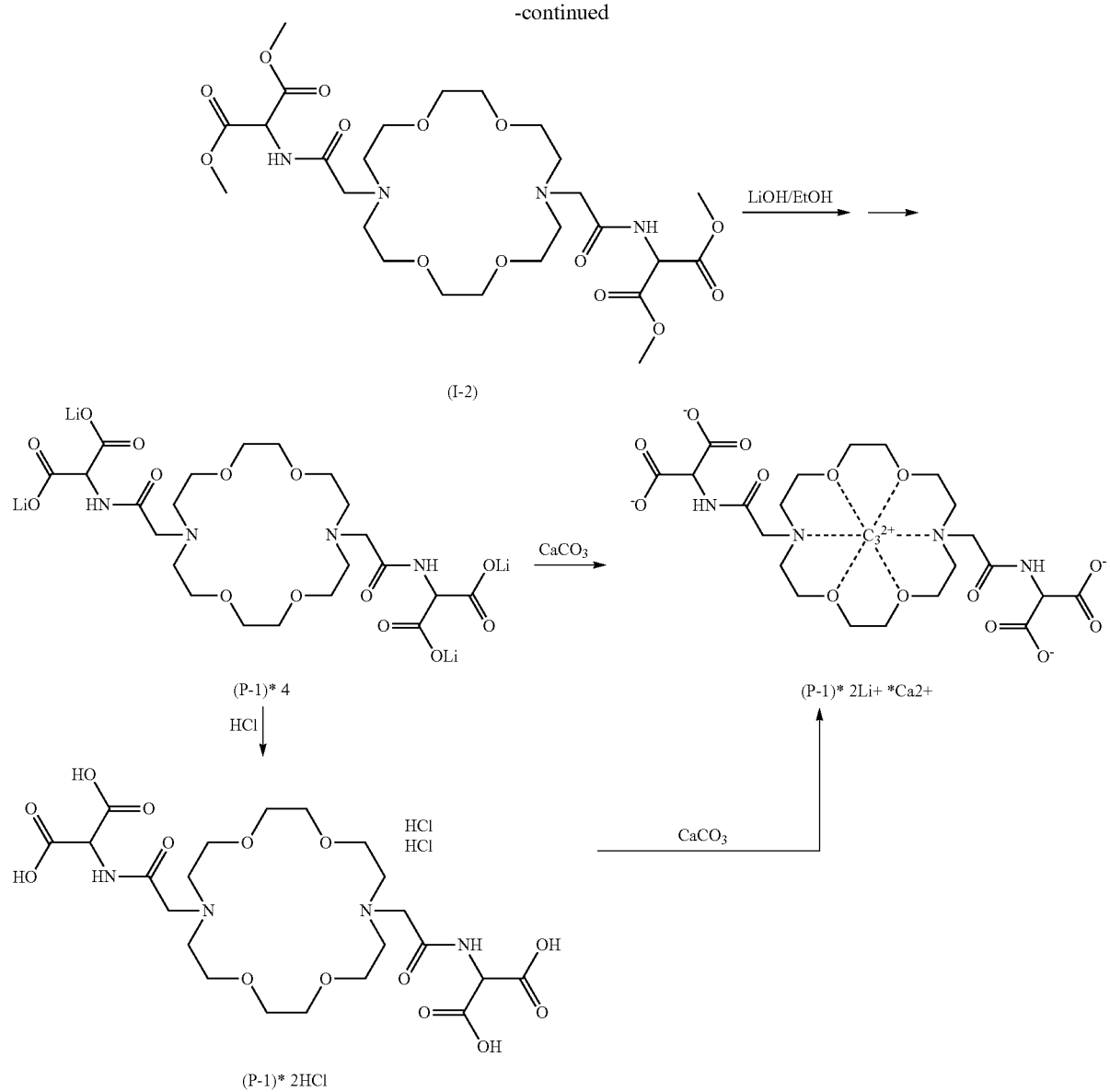
Route of synthesis B:

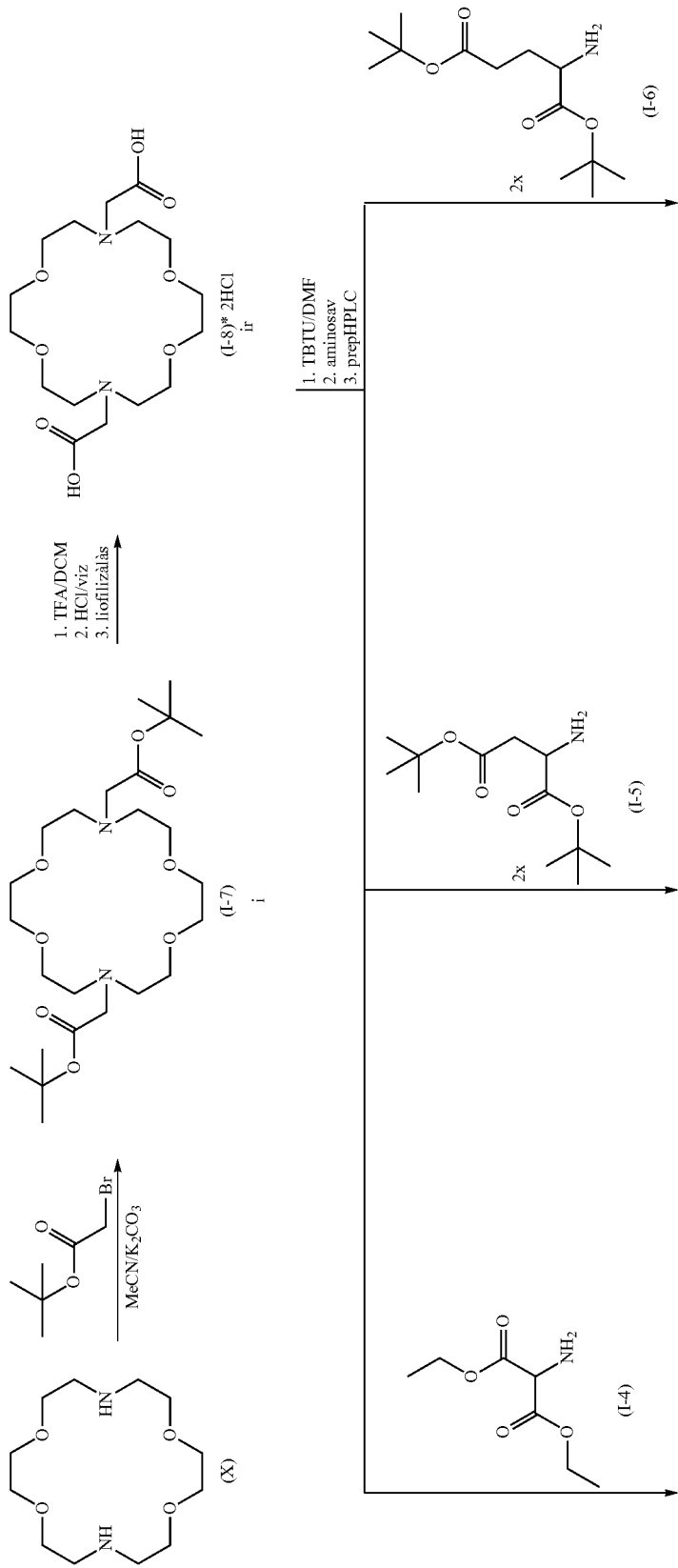

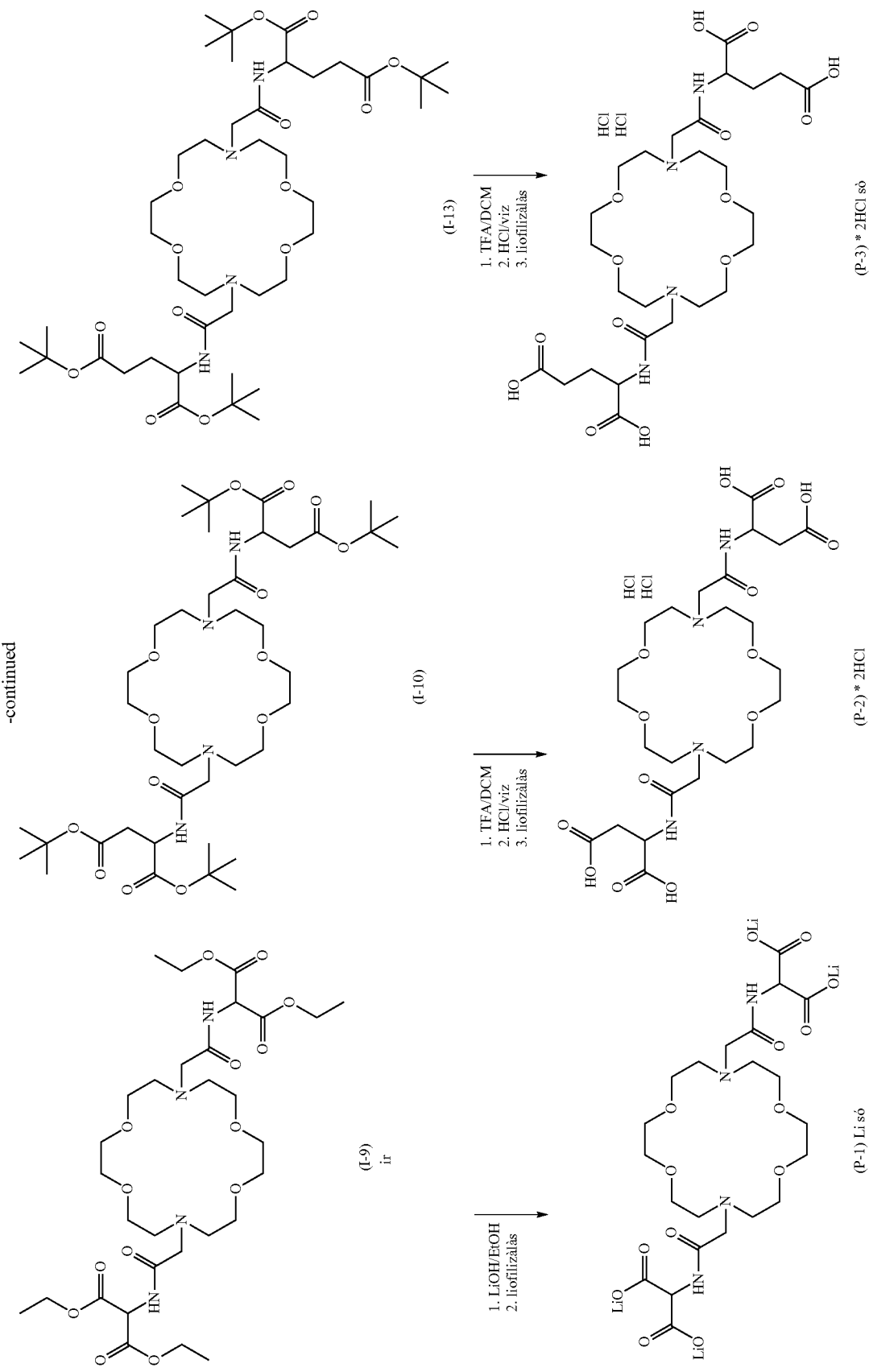

Route of Synthesis C:
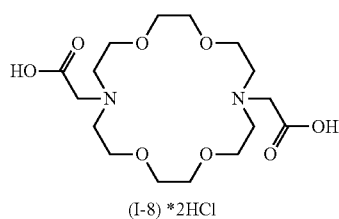
(I-8) *2HCl
1. TBTU/DMF
2. aminosav
3. prep HPLC
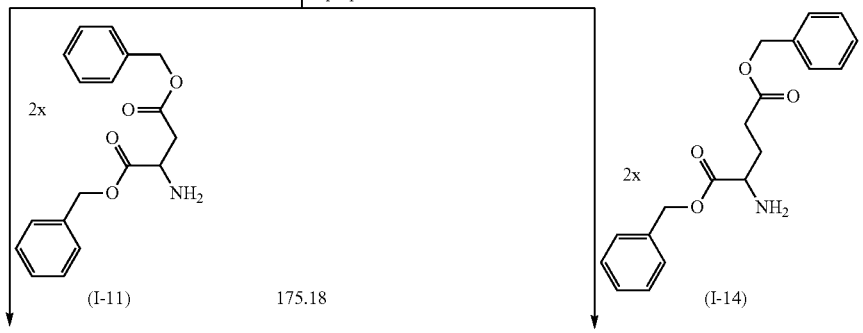
(I-11)   175.18   (I-14)
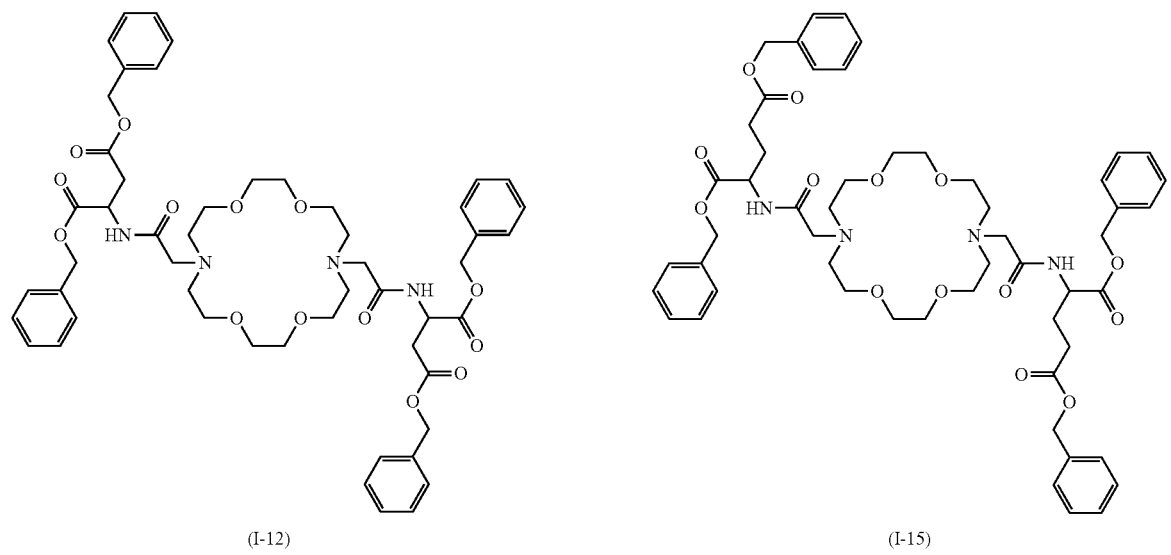
(I-12)   (I-15)
H$_2$/Pd/EtOH   H$_2$/Pd/EtOH

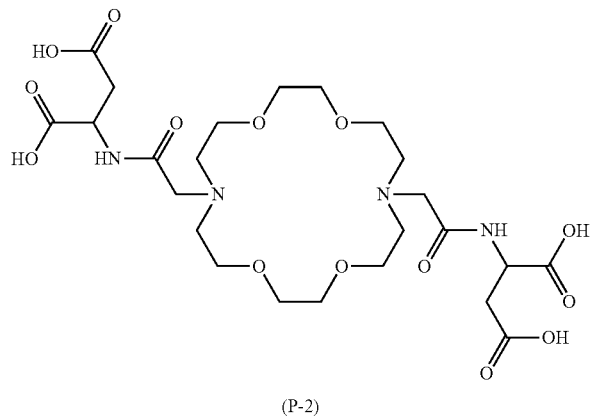

(P-2)

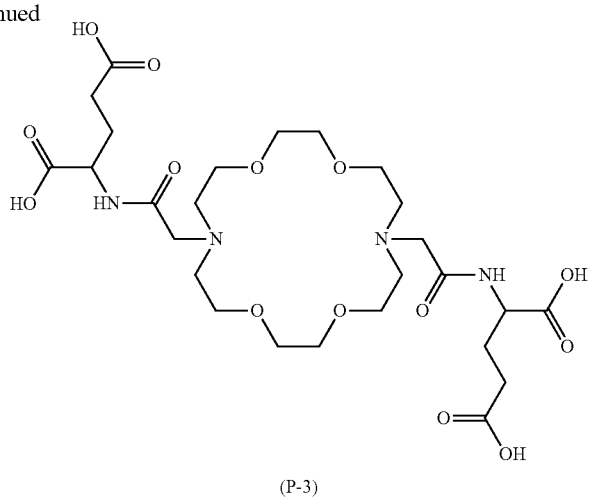

(P-3)

Víz=water
Aminosav=amino acid
Liofilizalas=lyophilisation
Só=salt

The compounds of the general formula (II/A) which can be used for the synthesis of the compounds of the general formula (I) can also be prepared in a manner that the carboxyl groups of the used amino dicarboxylic acid are protected with benzyl or other alkyl groups before the reaction, which groups are removed after the reaction. The N-acylation reaction can be preferably carried out with the use of acid halogenids or acid anhydrides. The reaction can be carried out in the presence of organic or inorganic base, preferably in the presence of potassium or sodium carbonate or triethylamine at a temperature between −20-+100° C., preferably between +20-+50° C.

The Kriptofix compound of the formula (X) can be alkylated with the thus obtained compounds of the general formula (II/A) or with a compound of the general formula (IV). The reaction can also be carried out in a manner that the reagents are reacted in the presence of an organic or inorganic base, preferably in the presence of potassium, sodium, cesium carbonate or triethyl amine, in an organic apolar or polar, aprotic or protic solvent, preferably in tetrahydrofurane, acretonitrile or dimethylformamide between a temperature of −20-+100° C., preferably between +50-+80° C.

If the alkylation is carried out with an alpha halogen carboxylic acid the result is a compound of the formula (IV) or a compound of the general formula (I).

The use of compounds of the formula (II/A) having protected carboxyl groups leads to the compound of the general formula (VII), meanwhile in case of using a protected compound of the general formula (IV) a compound of the general formula (V) is obtained.

The compound of the general formula (VI) can be prepared from the compound of the general formula (V) so that the compound of the general formula (V) is reacted in an aqueous or anhydrous, aprotic or protic solvent, preferably in dichloroethane with a strong organic or mineral acid, preferably in trifluoacetic acid at a temperature between −20-+100° C., preferably at room temperature if the group $R^{11}$ is e.g. an ester group.

The compound of the general formula (VII) can be prepared also in a way that the compound of the general formula (VI) is reacted with a compound of the general formula (IX) in the presence of organic or inorganic bases, preferably in the presence of triethylamine, in an organic polar or apolar solvent, preferably in tetrahydrofurane, acetonitrile, dimethylformamide, also in the presence of coupling agents of TBTU (O-(benzotriazol-1-yl)-N,N,N',N'-tetramethyluronium tetrafluoroborate), HATU (O-(7-azabenzotriazol-1-yl)-N,N,N', N'-tetramethyluronium hexafluorophosphate), TATU (2-(1H-7-Azabenzotriazol-1-yl)-1,1,3,3-tetramethyl uronium hexafluorophosphate), BOP ((Benzotriazol-1-yloxy)tris (dimethylamino)phosphonium hexafluorophosphate), PyBOP ((benzotriazol-1-yl-oxitripyrrolidinophosphonium hexafluorophosphate)), HOBT (hydroxybenztriazol) between a temperature of −20-+100° C., preferably between +50-+80° C. The reaction can be carried out in the presence other coupling agents such as dicyclohexylcarbodiimide or isobutylchloroformate as well.

The compound of the general formula (I) can also be prepared from the compound of the general formula (VII) in which the Q", Q', P" and P' groups stand for an ester group with acidic or alkaline hydrolysis. In case of the alkaline hydrolysis or the transformation to metal salt, the reaction can be carried out in a manner that the compound of the general formula (VII) is reacted in the presence of an inorganic base, preferably in the presence of potassium lithium, sodium or calcium carbonate, in organic polar or apolar, aprotic or protic solvent or possibly in an aqueous solvent, preferably in alcohols between a temperature of −20-+100° C., preferably between +50-+80° C.

With the evaporation of the solvent the salt is obtained, or alternatively, using an antisolvent it precipitates. Alternatively we can crystallise the salt from the evaporated reaction mixture, or the acid can be obtained with the acidification of the reaction mixture.

Esters according to the general formula (VII) can form into acid by the reaction with an acid, preferably hydrochloric acid in an aqueous or anhydrous, polar and apolar, aprotic and protic solvent, preferably in diethylether at a temperature between of −20-+100° C., preferably at room temperature.

In special cases the ester group can be removed by reduction. If Q", Q', P" and P' of the formula (VII) are benzyl or any other type of groups which can be removed by reduction, the reaction can be carried out in an aqueous or anhydrous, apolar or polar, aprotic or protic solvent, preferably in alcohols at a temperature between of −20-+100° C., preferably at room temperature, using transition metal catalysts, preferably Pd or Raney-Ni catalyst. As hydrogen source elemental hydrogen ammonium formiate, formic acid and hydrazine can also be used.

The processes described above are well-known for the person skilled in the art. As organic apolar solvents e.g. saturated or unsaturated hydrocarbons or mixtures thereof, e.g. hexane, heptane, toluene, diethyl ether can be used.

As polar aprotic solvent methylene chloride, tetrahydrofurane, dimethyl formamide, acetonitrile, dimethyl sulfoxide can also be used. As protic solvent water, aliphatic alcohols, such as methanol, ethanol, propanol, 2-propanol and the like can be used. The selection of the suitable solvents is the part of the general knowledge of the person skilled in the art.

Another object of the present invention is one of the key intermediates of the compound of the general formula (VII), wherein the meaning of n, X, $R^3$, $R^4$, $R^5$ and $R^6$ is as defined in claim 1, Q', Q'', P' and P'' are identical or different protected carboxyl groups, preferably ester, substituted or unsubstituted amide groups or cyano groups.

We wanted to verify the results of the calculations about the compounds of the present invention by measurements and verify also the fact whether the compounds are better complex-forming agents than the decorporol of the formula (XI).

Several different methods were tried unsuccessfully for the measuring of Ca ion and Sr ion complexing ability and the ratio between them. According to the information material the Sr ionselective electrode is not selective for Ca. We could not find differences between the Ca and Sr complexes with using 1H and 13C spectrums. Since the Ca and Sr nucleuses are not NMR active, therefore these could not be tested.

Therefore, the measurements of Ca—Sr ionselectivity were carried out with an AGILENT 6140 Octapol MS (mass spectrometer) equipped with an AGILENT 1200 HPLC. The ionization was carried out by using an electron-spray (ESI, MM-FS) soft ionization equipment with positive detection. During the measurements different complex-forming compounds of the formulas (P-1), P-2), (P-3) prepared with the synthesizes shown above and decorporol of the formula (XI) were added to stock solutions, then the solutions were measured with mass spectrometry. In the obtained spectrums the Sr and Ca complexes and the free complex-forming compounds could be clearly distinguished, which shows that the Sr binding ability of the three complex-forming agents of the present invention exceeds the ability of decorporol of the formula (XI) as follows:

| Complex-forming compounds | $Sr^{2+}/Ca^{2+}$ rate |
|---|---|
| (P-1) | 1.25 |
| (P-2) | 1.4 |
| (P-3) | 1.5 |
| Decorporol (XI) | 1.2 |

The peaks of free complex-forming compounds of the formulas (P-1), (P-2) and (P-3) are considerably smaller than the MS peaks of the Sr complexes. Their rate was lower in the case of decorporol, which shows its worse complex forming ability. It means that a considerable amount of decorporol does not form complex compounds but burdens the body as a ballast.

The decarboxylation, which is characteristic of decorporol, was shown also during the measurements. The experiments with different metal ions showed that the compound of (P-3) of the present invention binds the toxic metals ($Sr^{2+}$, $Sn^{2+}$, $Pd^{2+}$) significantly better than the physiologically important metals ($Zn^{2+}$, $Fe^{2+}$, $Ca^{2+}$). The behavior of Decorporol is similar, but binds the tin and palladium significantly less and in this case the amount of decarboxylated decorporol is much higher, meanwhile the compound of the formula (P-3) does not decarboxylate.

The decorporol binds Zn ions stronger than Ca ions, which can lead to the reduction of Zn ions to a dangerous extent.

The metal ion binding abilities of the compound of the formula (P-3) and Decorporol are as follows:

|  | (P-3) compound $M^{2+}/Ca^{2+}$ rate | Decorporol $M^{2+}/Ca^{2+}$ rate |
|---|---|---|
| Sr | 1.5 | 1.2 |
| Cu | 1.1 | 1.2(+1.5) |
| Zn | ca. 0 | 8(+4)* |
| Fe | ca. 0 | — |
| Sn | 100 | 22 |
| Pd | 29 | 20(+29 + 40)* |

*The peaks of decarboxylated fragments are in the brackets.

The metaboltic properties of the compounds of the formulas (P-1), (P-2) and (P-3) are presumably better because the whole or partial cleavage of the side chain releases amino or hydroxy acids, which are already present in the body. Furthermore, the solubility of the complex-forming compounds of the formulas (P-1), (P-2) and (P-3) is better compared to decorporol due to the more polar groups.

Therefore the compositions according to the present invention are suitable to remove the toxic metals from the body of patients who need such treatment, meanwhile the essential metal ions such as copper, zinc and calcium do not excrete from the body.

A further aspect of the present invention is a pharmaceutical composition, which comprises a compound of the general formula (I) as active ingredient, wherein the meaning of $R^1$ and $R^2$ is as defined above and the pharmaceutically acceptable salts and/or complexes thereof beside the usual carrier agents.

The most advantageous embodiment of the present invention comprises as active ingredient a compound of (P-2), (P-1) or (P-3), or a salt and/or complex thereof. According to the advantageous embodiment of the present invention the pharmaceutical composition comprises 0.01-95 weight %, preferably 1-50 weight %, practically 5-30 weight % of the active ingredient.

The pharmaceutical compositions according to the present invention are suitable for peroral, parenteral, rectal or topical treatments. The pharmaceutical compositions can be solid or liquid and suitable for peroral, parenteral, rectalor topical treatments.

The peroral solid compositions can be powders, capsules, tablets, film coated tablets, microcapsules etc., which can contain as carrier binders, e.g. gelatin. sorbitol, polyvinylpyrolidone etc, diluents such as lactose, glucose, starch, potassium phosphate etc., tableting accessories such as magnesium stearate, talc, polyethylene glycol, silica etc., wetting agents such as sodium lauryl sulphate etc. The peroral liquid compositions can be solutions, suspensions or emulsions, which can contain as carrier suspending agents, e.g. gelatin, carboxymethylcellulose etc., emulsifying agents such as sorbitane monooleate etc.; solvents, such as water oils, glycerol, propyleneglycol, ethanol; preservatives, such as p-hydroxybenzoic acid methyl or propyl ester etc. The parenteral compositions generally are a sterile solution of the active ingredient. The above-mentioned and other pharmaceutical formulations are known, see for example the handbook of Remington's Pharmaceutical Sciences, edition 18, Mack Publishing Co., Easton, USA (1990).

In most of the cases the pharmaceutical composition contains unit dosage forms. A typical daily dose for an adult patient is 0.1-3000 mg of the compound of the general formula (I) or a pharmaceutically active salt and/or complex based on 1 kg bodyweight. The daily dose can be administered in one or in several parts. The dose depends on several factors and is determined by the physician.

The pharmaceutical composition comprising a compound of the general formula (I) or salts and/or complexes thereof and one or more carriers can be prepared by the mixing of the active ingredient and one or more carriers, then the mixture is formed to a pharmaceutical composition in a known manner. Suitable processes are known from the literature, e.g. from the above mentioned Remington's Pharmaceutical Sciences handbook.

- An advantage of the present invention is that the compounds of the general formula (I) bind the toxic metals such as palladium, strontium, tin, lead stronger than the Decorporol, thus reducing the effective doses and the burden of the excretory system of the body is also smaller.
- The water solubility of the compounds of the general formula (I) is better than that of the earlier known compounds. More concentrated infusion solutions can be prepared, the necessary amount of the compound can be administered more quickly to the person who needs it.
- The salts of the compound of the general formula (I) are easy to be prepared, purified and are more stable than the neutral form of these compounds according to the prior art.
- During the metabolism of the compounds of the general formula (I) according to the present invention hydroxy acids and amino acids are formed which are not toxic.
- According to the tests they bind more effectively the harmful ions than the decroporol.
- The catastrophe management needs to finance the storage of less compounds.

BRIEF DESCRIPTION OF DRAWINGS

Our invention is shown particularly in the Examples below, without limiting the scope of the invention to the Examples:

On the Drawings the metal ion binding properties of the complex compounds of the present invention and decorporol (XI) measured with HPLC-MS equipment are shown as follows:

Drawing 1, FIG. 1-A: The compound of (P-1) $Ca^{2+}$ and $Sr^{2+}$ ions.

Drawing 1, FIG. 1-B: The compound of (P-2) $Ca^{2+}$ and $Sr^{2+}$ ions.

Drawing 2, FIG. 2-A: The compound of (P-3) $Ca^{2+}$ and $Sr^{2+}$ ions.

Drawing 2, FIG. 2-B: Decorporol (XI) $Ca^{2+}$ and $Sr^{2+}$ ions.

Drawing 3, FIG. 3-A: The compound of (P-3) $Ca^{2+}$ and $Cu^{2+}$ ions.

Drawing 3, FIG. 3-B: Decorporol (XI) $Ca^{2+}$ and $Cu^{2+}$ ions.

Drawing 4, FIG. 4-A: The compound of (P-3) $Ca^{2+}$ and $Zn^{2+}$ ions.

Drawing 4, FIG. 4-B: Decorporol (XI) $Ca^{2+}$ and $Zn^{2+}$ ions.

Drawing 5, FIG. 5-A: The compound of (P-3) molekula $Ca^{2+}$ and $Pb^{2+}$ ions.

Drawing 5, FIG. 5-B: Decorporol (XI) $Ca^{2+}$ and $Pb^{2+}$ ions.

Drawing 6, FIG. 6-A: The compound of (P-3) $Ca^{2+}$ and $Sn^{2+}$ ions.

Drawing 6, FIG. 6-B: Decorporol (XI) $Ca^{2+}$ and $Sn^{2+}$ ions.

Drawing 7, FIG. 7-A: The compound of (P-3) $Ca^{2+}$ and $Fe^{2+}$ ions.

The preparation and tests thereof are particularly shown in the examples below without limiting our claims to the examples:

GENERAL METHODS

To follow the course of the reactions and the analytical examination of the products an AGILENT 1200 HPLC device was used, which was equipped beside the usual UV detector also with an AGILENT 6140 Quadrupol MS detector. The structures of the compounds were identified using a BRUKER AVANCE 400 MHz NMR equipment. For the purification of the product two different methods were used. The compounds prepared in a larger amount and having protecting groups were purified with an automated flash chromatograph on a column containing 120 g of normal silica (Kiesel gel 60; 0,063-0,100 mM). The sample was evaporated onto the surface of silica gel having a volume three times higher than that of the compound using dichloromethane. During the process the rate of the heptane and ethyl acetate used as eluents was changed according to a prewritten gradient program, which was differing from substance to substance. For detection UV detector was used. For the purification of the final intermediates a preparative HPLC equipped with a UV detector was used, and the used 250×50 mm HPLC column was filled with a reverse-phase packing of 10 um PHENOMENEX GEMINI.

PREPARATIVE EXAMPLES

Route of Synthesis A

Example A.1

Preparation of 2-(2-Chloro-acetylamino)-malonic acid dimethyl-ester (I-1)

General Formula II/A

In 200 ml of acetonitrile 18.3 g of dimethyl aminomalonate hydrochloride were suspended in the presence of 20.58 ml of triethylamine, 12.07 ml of chloroacetyl chloride were added dropwise during 10 minutes under vigorous stirring. The mixture was stirred for additional ten minutes, then evaporated and dissolved in a mixture of ethyl acetate (300 ml) and saturated sodium carbonate solution (100 ml). The organic phase is washed once with 100 ml of saturated sodium carbonate solution, then twice with 50 ml of saturated sodium chloride solution, then dried over magnesium sulphate, filtered, washed with ethyl acetate and evaporated under vacuum. The product is 21.1 g (white crystalline product 90.1%).

Example A. 2

Preparation of 2-[2-(16-{[(Bis-methoxycarbonyl-methyl)-carbamoyl]-methyl}-1,4,10,13-tetraoxa-7,16-diaza-cyclooctadec-7-yl)-acetylamino]-malonic acid dimethyl-ester (I-2)

General Formula VII

In 150 ml of acetonitrile, 5.0 g of kriptofix (X), 10.46 g of 2-(2-chloro-acetylamino)-malonic acid dimethyl ester (I-1) and 5.26 g of potassium carbonate were suspended and kept under vigorous stirring for 3 days at 80° C. The progress of the reaction was monitored by HPLC-MS. After the conversion rate has reached 70%, the reaction mixture is evaporated and dissolved in a mixture of 200 ml of ethyl acetate and 60 ml of saturated potassium carbonate solution. The organic phase is washed once with 60 ml of saturated sodium carbonate solution, then with 50 ml of saturated sodium chloride solution, then dried over magnesium sulphate, filtered, washed with ethyl acetate and evaporated under vacuum. The crude product is 16 g. The crude product was purified on silica with a mixture of DMC:MeOH (DCM: dichloromethane). The obtained product is 5.2 g (white oil, 40.4%).

Example A.3

Preparation of 2-(2-{16-[(Dicarboxymethyl-carbamoyl)-methyl]-1,4,10,13-tetraoxa-7,16-diaza-cyclooctadec-7-yl}-acetylamino)-malonic acid tetralithium salt/(P-1)*4 Li$^+$/ (General formula I)

In 50 ml of methanol 5.0 g of the compound of the formula (I-2) prepared according to Example A.2., and 1.49 g of LiOH were suspended under vigorous stirring and were kept at 68° C. for an hour. The progress of the reaction was monitored by HPLC-MS. The reaction mixture is evaporated and the residue is suspended in ether and filtered. The product is 4.5 g (brown crude product). The crude product was purified with preparative HPLC in a mixture of MeCN:water. The obtained solution was lyophilized. Thus 3.9 g of titled product are obtained (off-white product, 70%).

Example A.4

Preparation of 2-(2-{16-[(Dicarboxymethyl-carbamoyl)-methyl]-1,4,10,13-tetraoxa-7,16-diaza-cyclooctadec-7-yl}-acetylamino)-malonic acid dilithium calcium salt/(P-1)*2 Li$^+$*Ca$^{2+}$/ (General formula I)

In 50 ml of methanol, 3.0 g of the compound of formula/(P-1)*4 Li/ prepared according to the Example A.3. and 2.48 g of calcium carbonate are suspended and kept at 50° C. under vigorous stirring for an hour. The product is filtered off and dried. The product is 3.6 g (brown, 90%).

Example A.5

Preparation of 2-(2-{16-[(Dicarboxymethyl-carbamoyl)-methyl]-1,4,10,13-tetraoxa-7,16-diaza-cyclooctadec-7-yl}-acetylamino)-malonic acid dihydrochloride salt/(P-1)*2 HCl/ (General formula I)

In 20 ml of ether 1.2 g of the compound of the formula/(P-1)*4 Li/ prepared according to the Example A.3. were suspended and 1.2 ml of dioxane containing HCl were added under vigorous stirring. The precipitated product is filtered, washed with ether and dried. Thus, 1.2 g of titled, strongly hygroscopic, product is obtained (Yield: 85%).

Example A.6

Preparation of 2-(2-{16-[(Dicarboxymethyl-carbamoyl)-methyl]-1,4,10,13-tetraoxa-7,16-diaza-cyclooctadec-7-yl}-acetylamino)-malonic acid dicalcium salt/(P-1)*2 Ca$^{2+}$/ (General formula (I))

In 10 ml of methanol 0.4 g of the dihydrochloride salt/(P-1)*2 HCl/ prepared according to the Example A.5. and 0.5 g of calcium carbonate were suspended and kept at 50° C. for an hour under vigorous stirring. The precipitated product was filtered, washed with ether and dried. Thus 0.6 g of titled off-white crystalline product is obtained.

Using analog synthesizes we have prepared the following derivatives with the yields as follows:

| Sign | chemical name | Yield |
|---|---|---|
| (P-1)* 4 Li$^+$ | 2-(2-{16-[(Dicarboxymethyl-carbamoyl)-methyl]-1,4,10,13-tetraoxa-7,16-diaza-cyclooctadec-7-yl}-acetylamino)-malonic acid tetralithium salt | 25.4% |
| (P-1) * 2 Li$^+$ *Ca$^{2+}$ | 2-(2-{16-[(Dicarboxymethyl-carbamoyl)-methyl]-1,4,10,13-tetraoxa-7,16-diaza-cyclooctadec-7-yl}-acetylamino)-malonic acid dilithium calcium salt | 19.1% |
| (P-2) * 4 Li$^+$ | 2-(2-{16-[(1,2-Dicarboxy-ethylcarbamoyl)-methyl]-1,4,10,13-tetraoxa-7,16-diaza-cyclooctadec-7-yl}-acetylamino)-succinic acid tetralithium salt | 29.5% |
| (P-3) * 4 Li$^+$ | 2-(2-{16-[(1,3-Dicarboxy-propylcarbamoyl)-methyl]-1,4,10,13-tetraoxa-7,16-diaza-cyclooctadec-7-yl}-acetylamino)-glutaric acid tetralithium salt | 32.3% |

Route of Synthesis B

Example B.1

Preparation of (16-tert-Butoxycarbonylmethyl-1,4,10,13-tetraoxa-7,16-diaza-cyclooctadec-7-yl)-acetic acid tert-butyl ester (I-7)

General Formula V

In 150 ml of acetonitrile 5.0 g of kriptofix of the formula (X), 8.18 g of bromoacetic acid tert.butyl ester and 5.26 g of potassium carbonate were suspended and then kept at 80° C. for 2 days under vigorous stirring. The progress of the reaction was monitored by HPLC-MS. After the conversion rate has reached 100% the reaction mixture is evaporated and dissolved in a mixture of 200 ml of ethyl acetate and 60 ml of saturated sodium carbonate solution. The organic phase is washed once with 60 ml of saturated sodium carbonate solution and with 50 ml of saturated sodium chloride solution, then dried over sodium sulphate and filtered, washed with ethylacetate, then evaporated in vacuum. Thus 6.6 g crude product are obtained. The crude product is purified on silica in a mixture of DCM:MeOH. Thus 5.6 g of titled white oil are obtained. (Yield is 60.2%)

Example B.2

Preparation of (16-carboxymethyl-1,4,10,13-tetraoxa-7,16-diaza-cyclooctadec-7-yl)-acetic acid dihydrochloride/(I-8)*2HCl/ (general formula VI)

In 70 ml of dichloromethane (DCM) 5.6 g of the tert butyl derivative of the formula (I-7) prepared according to the Example B.1. are dissolved and 50 ml of trifluoro acetic acid are added to the solution under vigorous stirring. The mixture is kept at room temperature for an hour. The progress of the reaction is monitored by HPLC-MS. After the conversion rate has reached 100% the reaction mixture is evaporated to dry. The residue is diluted with 100 ml of water and 5 ml of 1 N hydrochloric solution are added then lyophilized. Thus 4.2 g of titled oily product are obtained.

Example B.3

Preparation of 2-[2-(16-{[(Bis-ethoxycarbonyl-methyl)-carbamoyl]-methyl}-1,4,10,13-tetraoxa-7,16-diaza-cyclooctadec-7-yl)-acetylamino]-malonic acid diethyl ester (I-9) (general formula VII)

In 20 ml of dimethylformamide 1.0 g of the compound prepared according to the Example B.2./(I-8)*2HCl/ is dissolved and in the presence of 1.14 g of diisopropyl-ethylamine 1.42 g of N,N,N',N'-tetramethyl-O-(benzotriazol-1-yl)uronium tetrafluoroborate (TBTU) are added to the mixture. After 30 minutes stirring 0.85 g of diethyl-1-aminomalonate of the formula (I-4) are added to the mixture and the stirring is followed for a further day at room temperature. The progress of the reaction is monitored by HPLC-MS. After the conversion has reached 80-90% the reaction mixture is evaporated and purified with preparative HPLC then lyophilized. Thus 4.4 g of titled product are obtained.

NMR 1H (ppm): 1.19 (OEt, 12H, t, 7.0 Hz); 2.76 (NCH2, 8H, t, 5.6 Hz); 3.20 (NCH2CO, 4H, s); 3.53 (OCH2, 16H, m); 4.15 (OEt, 8H, q, 7 Hz); 5.05 (CH, 2H, d, 4 Hz); 8.42 (NH, 2H, d, 4 Hz);

HPLC-MS (M+H$^+$): 693.1 Da

Example B.4

Preparation of 2-(2-{16-[(Dicarboxymethyl-carbamoyl)-methyl]-1,4,10,13-tetraoxa-7,16-diaza-cyclooctadec-7-yl}-acetylamino)-malonic acid tetralithium salt/(P-1)*4 Li$^+$/ (General formula I)

In 20 ml of ethanol 0.6 g of the ethyl ester compound of the formula (I-9) prepared according to Example B.3. are dissolved and 0.16 g lithiumhydroxide is added to the solution and stirred for 30 minutes at 40° C. The progress of the reaction is monitored by HPLC-MS. The reaction mixture is evaporated, diluted with water, then lyophilized. Thus 0.4 g of titled compound are obtained.

NMR 1H (ppm): 2.75 (NCH2, 8H, m); 3.20 (NCH2CO, 4H, s); 3.30 (OCH2, 16H, m); 4.84 (CH, 2H, d, 4 Hz); 8.38 (NH, 2H, d, 4 Hz);

HPLC-MS (M+H$^+$): 581.1 Da

Example B.5

Process of 2-(2-{16-[(1,2-Bis-tert-butoxycarbonyl-ethylcarbamoyl)-methyl]-1,4,10,13-tetraoxa-7,16-diaza-cyclooctadec-7-yl}-acetylamino)-succinic acid di-tert-butyl ester (I-10) (General formula VII)

In 20 ml of dimethylformamide 1.0 g of a compound of the formula/(I-8)*2HCl/ prepared according to Example B.2. and in the presence of 1.14 g diisopropyl-ethylamine 1.42 g of N,N,N',N'-tetramethyl-O-(benzotriazol-1-yl)uronium tetrafluoroborate (TBTU) are added. After 30 minutes stirring 1.20 g of di-tert-butyl-aspartate of the formula (I-5) are added and the mixture is stirred for an additional day at room temperature. The progress of the reaction is monitored by HPLC-MS. After the conversion has reached 80-90%, the reaction mixture is purified by preparative HPLC, then lyophilized. Thus 120 mg of titled product are obtained.

NMR 1H (ppm): 1.44 (tBu, 36H, s); 2.65 (CH, 2H, m); 2.75 (CH2, 8H, m); 3.16 (NCH2CO, 4H, s); 3.30 (OCH2, 8H, m); 3.54 (OCH2, 8H, m); 4.52 (CH2, 4H, d); 8.20 (NH, 2H, d, 4 Hz);

HPLC-MS (M+H$^+$): 833.1 Da

Example B.6

Preparation of 2-(2-{16-[(1,2-Dicarboxy-ethylcarbamoyl)-methyl]-1,4,10,13-tetraoxa-7,16-diaza-cyclooctadec-7-yl}-acetylamino)-succinic acid dihydrochloride salt/(P-2)*2HCl/ (General formula I)

In 5 ml of dichloromethane is dissolved 120 mg of a tert-.butyl ester of the formula (I-10) prepared according to the Example B.5. and 5 ml of trifluoroacetic acid is added, then stirred for 30 minutes. The progress of the reaction is monitored by HPLC-MS. The reaction mixture is evaporated, diluted with water and 2 ml of 1 N hydrochloride solution is added, then lyophilized. Thus 60 mg of titled compound are obtained.

NMR 1H (ppm): 2.65 (CH, 2H, m); 2.75 (CH2, 8H, m); 3.30 (OCH2, 12H, m, overlaps with water); 3.54 (OCH2, 8H, m); 4.5 (CH2, 4H, d); 8.10 (NH, 2H, d, 4 Hz);

HPLC-MS (M+H$^+$): 609.1 Da

Example B.7

Preparation of 2-(2-{16-[(1,3-Bis-tert-butoxycarbonyl-propylcarbamoyl)-methyl]-1,4,10,13-tetraoxa-7,16-diaza-cyclooctadec-7-yl}-acetylamino) aspartic acid di-tert-butyl ester (I-13) (General formula VII)

In 20 ml dimethylformamide 1.0 g of the compound of the formula/(I-8)*2HCl/ prepared according to the Example B.2. and in the presence of 1.14 g of diisopropyl-ethylamine 1.42 g of N,N,N',N'-tetramethyl-O-(benzotriazol-1-yl)uronium tetrafluoroborate (TBTU) are added. After 30 minutes stirring 1.26 g of di-tert-butil-glutaminate of the formula (I-6) are added to the mixture and stirred for one day at room temperature. The progress of the reaction is monitored by HPLC-MS. After the conversion has reached 80-90%, the reaction mixture is purified with preparative HPLC, then lyophilized. Thus 800 mg of titled product are obtained.

NMR 1H (ppm): 1.44 (tBu, 36H, s); 1.32 (CH2, 2H, m); 1.97 (CH2, 2H, m); 2.23 (CH, 2H, m); 2.72 (CH2, 8H, m); 3.11 (NCH2CO, 4H, s); 3.30 (OCH2, 8H, m, under water); 3.53 (OCH2, 8H, m); 4.18 (CH2, 2H, m); 7.93 (NH, 2H, d, 4 Hz);

HPLC-MS (M+H$^+$): 861.1 Da

Example B.8

Preparation of 2-(2-{16-[(1,3-Dicarboxy-propylcarbamoyl)-methyl]-1,4,10,13-tetraoxa-7,16-diaza-cyclooctadec-7-yl}-acetylamino) glutaric acid dihydrochloride salt/(P-3)*2HCl/ (General formula I)

In 5 ml of dichloromethane 800 mg of tert butyl ester compound of the formula (I-13) prepared according to the Example B.7. are dissolved and 5 ml of trifluoroacetic acid are added to the mixture and stirred for 30 minutes at room temperature. The progress of the reaction is monitored by HPLC-MS. The reaction mixture is evaporated, diluted with water and 2 ml of 1 N hydrochloric acid are added, then lyophilized. Thus 420 mg of titled compound are obtained.

NMR 1H (ppm): 1.34 (CH2, 2H, m); 2.02 (CH2, 2H, m); 2.23 (CH, 2H, m); 3.1-3.5 (OCH2, 24H, m,); 4.05 (CH2, 2H, m); 8.00 (NH, 2H, d, 4 Hz); 9.5; 13;

HPLC-MS (M+H$^+$): 637.0 Da

Route of Synthesis C

Example C.1

Preparation of 2-(2-{16-[(1,2-Bis-benzyloxycarbonyl-ethylcarbamoyl)-methyl]-1,4,10,13-tetraoxa-7,16-diaza-cyclooctadec-7-yl}-acetylamino)succinic acid dibenzyl ester (I-12) (General formula VII)

is dissolved

In 20 ml of dimethylformamide 1.0 g of the compound of the formula/(I-8)*2HCl/ prepared according to the Example B.2. and in the presence of 1.14 g diisopropyl-ethylamine 1.42 g of N,N,N',N'-tetramethyl-O-(benzotriazol-1-yl)uronium tetrafluoroborate (TBTU) are added. After 30 minutes stirring 1.56 g dibenzyl-aspartate tosylate salt of the formula (I-11) is added and the mixture is stirred for a day at room temperature. The progress of the reaction is monitored by HPLC-MS. After the conversion has reached 80-90% the reaction mixture is purified with preparative HPLC then lyophilized. Thus 110 mg of titled compound are obtained.

NMR 1H (ppm): 2.54 (CH, 2H, m, under DMSO); 2.75 (CH2, 8H, m); 3.16 (NCH2CO, 4H, s); 3.30 (OCH2, 8H, m, also water); 3.50 (OCH2, 8H, m); 4.50 (CH2, 4H, d); 7.41 (Ph, 20h, m); 8.20 (NH, 2H, d, 4 Hz);

HPLC-MS (M+H$^+$): 970.2 Da

Example C.2

Preparation of 2-(2-{16-[(1,2-Dicarboxy-ethylcarbamoil)-methyl]-1,4,10,13-tetraoxa-7,16-diaza-cyclooctadec-7-yl}-acetylamino)-succinic acid (P-2) (General formula I)

In 10 ml of ethanol 110 mg of benzyl ester compound of the formula of (I-12) prepared according to the Example C.1. are dissolved and 50 mg of Pd(C) are added to the mixture. The mixture is stirred for 18 hours under a pressure of 4 bar of hydrogen at room temperature. The progress of the reaction is monitored by HPLC-MS. The reaction mixture is evaporated. Thus 100 mg of titled compounds are obtained.

NMR 1H (ppm): 2.65 (CH, 2H, m); 2.75 (CH2, 8H, m); 3.30 (OCH2, 12H, m, overlaps with water); 3.54 (OCH2, 8H, m); 4.5 (CH2, 4H, d); 8.10 (NH, 2H, d, 4 Hz); (of pour quality), HPLC-MS (M+H$^+$): 609.1 Da Example C.3

Preparation of 2-(2-{16-[(1,3-Bis-benzyloxycarbonyl-propylcarbamoyl)-methyl]-1,4,10,13-tetraoxa-7,16-diaza-cyclooctadec-7-yl}-acetylamino)-glutaric acid dibenzyl ester (I-15) (General formula VII)

In 20 ml of dimethylformamide 1.0 g of the compound of the formula/(I-8)*2HCl/ prepared according to the Example B.2. and in the presence of 1.14 g diisopropyl-ethylamine 1.42 g of N,N,N',N'-tetramethyl-O-(benzotriazol-1-yl)uronium tetrafluoroborate (TBTU) are added to the mixture. After 30 minutes stirring 1.6 g of dibenzyl-glutamic acide tosylate salt of the formula (I-14) are added and the mixture is stirred for one additional day. The progress of the reaction is monitored by HPLC-MS. After the conversion has reached 80-90%, the reaction mixture is purified with preparative HPLC, then lyophilized. Thus 800 mg of titled compound are obtained.

NMR 1H (ppm): 1.82 (CH2, 2H, m); 2.12 (CH2, 2H, m); 2.50 (CH, 2H, m, under DMSO); 3.2-3.5 (24H, under water); 4.12 (CH2, 2H, m); 4.44 (CH2, 2H, m); 7.41 (Ph, 20h, m); 8.00 (NH, 2H, d, 4 Hz);

HPLC-MS (M+H$^+$): 998.2 Da

Example C.4

Preparation of 2-(2-{16-[(1,3-Dicarboxy-propylcarbamoyl)-methyl]-1,4,10,13-tetraoxa-7,16-diaza-cyclooctadec-7-yl}-acetylamino)-pentanedioic acid (P-3) (General formula I)

In 5 ml of dichloromethane 800 mg of benzyl ester compound according to the formula (I-15) prepared according to the Example C.3. are dissolved and 5 ml of trifluoroacetic acid are added to the mixture, then stirred for 30 minutes at room temperature. The progress of the reaction is monitored by HPLC-MS. The reaction mixture is evaporated, diluted with water and 2 ml of 1 N hydrochloric acid are added, then lyophilized. Thus 500 mg of titled compound are obtained.

NMR 1H (ppm): 1.34 (CH2, 2H, m); 2.02 (CH2, 2H, m); 2.23 (CH, 2H, m); 3.1-3.5 (OCH2, 24H, m, under water); 4.05 (CH2, 2H, m); 8.00 (NH, 2H, d, 4 Hz); 9.5; 13;

HPLC-MS (M+H$^+$): 637.0 Da

Analytical Examinations:

Measurement of Metal Selectivity:

Several different methods were tried unsuccessfully for the measuring of Ca ion and Sr ion complexing ability and the ratio between them. According to the information material the Sr ionselective electrode is not selective for Ca. We could not find differences between the Ca and Sr complexes with using 1H and 13C spectrums. Since the Ca and Sr nucleuses are not NMR active, therefore these could not be tested.

The measuring of Ca—Sr ionselectivity was carried out with an AGILENT 6140 Octapol MS (mass spectrometer) equipped with an AGILENT 1200 HPLC. The ionization was carried out by using an electron-spray (ESI, MM-FS) soft ionization equipment with positive detection. The used field strength was 10000V, the spray temperature 220° C., Fragmentor: 70; Treshold: 500, stepsize 0.2 Da; Ionization Switch Delay: 0 ms; Polarity Switch Delay 300 ms; Gain: 1:0; Mass range: 100-1200 Da. Nitrogen gas was used. These parameters were obtained by optimization. The used HPLC column was a 30 mm long WATERS ACQUITY UPLC column with an inner diameter of 2.1 mm and filled with C18 packing of 1.8 um. The amounts of the injected samples were changed between 2-10 ul. The eluents used due to the appropriate ionization were as follows:

Eluent A: 0.395 g of NH4HCO3 dissolved in 1 l water+50 ml MeCN.

Eluent B: MeCN

The Compositions of the Used Stock Solutions:

Solution A: 0.1 M Ca ion stock solution: 222.1 mg (2 mmol) of anhydrous $CaCl_2$ are dissolved in 20 ml of distilled water.

Solution B: 0.1 M Sr ion stock solution: 533.5 mg (2 mmol) of $SrCl_2.6H_2O$ are dissolved in 20 ml of distilled water.

Solution C: 0.1 M Cu ion stock solution: 500.0 mg (2 mmol) of $CuSO_4.5H_2O$ are dissolved in 20 ml of distilled water.

Solution D: 0.1 M Zn ion stock solution: 272.5 mg (2 mmol) of $ZnCl_2$ are dissolved in 20 ml of distilled water.

Solution E: 0.1 M Sn ion stock solution: 379.6 mg (2 mmol) of $SnCl_2$ are dissolved in 20 ml of distillated water.
Solution F: 0.1 M Pb ion stock solution: 217.0 mg (2 mmol) of $Pb(OOCCF_3)_2$ are dissolved in 5 ml distilled water.
Solution G: 0.1 M Fe ion stock solution: 360.0 mg (2 mmol) of $Fe(NO_3)_2$ are dissolved in 20 ml distilled water.

From the compounds according to the present invention the following compounds were tested:

2-(2-{16-[(Dicarboxymethyl-carbamoyl)-methyl]-1,4,10, 13-tetraoxa-7,16-diaza-cyclooctadec-7-yl}-acetylamino)-malonic acid tetralithium salt/(P-1)*4Li$^+$/: In the analytical part it is called hereinafter as (P-1). The (P-1)*4Li$^+$ salt was prepared according to the Example B.4.

2-(2-{16-[(1,2-Dicarboxy-ethylkarbamoyl)-methyl]-1,4, 10,13-tetraoxa-7,16-diaza-cyclooctadec-7-yl}-acetylamino)-succinic acid (P-2), which was prepared according to Example C.2.

2-(2-{16-[(1,3-Dicarboxy-propylcarbamoyl)-methyl]-1, 4,10,13-tetraoxa-7,16-diaza-cyclooctadec-7-yl}-acetylamino)-pentanedioic acid (P-3), which was prepared according to Example C.4.

Furthermore the Decorporol of the formula (XI) was examined as reference.

Solution I: 1. Complex-forming stock solution (1.5 mM): 2.1 mg of the compound/(P-1)*4Li$^+$/: (3.01 μmol) are dissolved in 2 ml distilled water.
Solution II: 2. Complex-forming stock solution (1.5 mM): 2.0 mg of the compound (P-2) (2.89 μmol) are dissolved in 2 ml distilled water.
Solution III: 3. Complex-forming stock solution (1.5 mM): 2.2 mg of the compound (P-3) (3.10 μmol) are dissolved in 2 ml distilled water.
Solution IV: 4. Complex-forming stock solution (1.5 mM; Decorporol, LB-145/of the formula (XI)/: 2.0 mg of LB-145 (3.4 μmol) are dissolved in 2 ml distilled water.

Preparation of Standard Solutions:

100 μl of A stock solution and to 100 μl of I, II, III or IV solutions 100 μl of B-G solution are added according to the Table below and the amount of the thus obtained samples are completed to 1 ml, then injected into the HPLC.

Measuring Table: The preparation of standard solutions of 1-14.

| No. | 1. stock solution | 2. stock solution | 3. stock solution |
|---|---|---|---|
| 1 | 100 μl of A solution | 100 μl of I solution | 100 μl of B solution |
| 2 | 100 μl of A solution | 100 μl of II solution | 100 μl of B solution |
| 3 | 100 μl of A solution | 100 μl of III solution | 100 μl of B solution |
| 4 | 100 μl of A solution | 100 μl of IV solution | 100 μl of B solution |
| 5 | 100 μl of A solution | 100 μl of III solution | 100 μl of C solution |
| 6 | 100 μl of A solution | 100 μl of III solution | 100 μl of D solution |
| 7 | 100 μl of A solution | 100 μl of III solution | 100 μl of E solution |
| 8 | 100 μl of A solution | 100 μl of III solution | 100 μl of F solution |
| 9 | 100 μl of A solution | 100 μl of III solution | 100 μl of G solution |
| 10 | 100 μl of A solution | 100 μl of IV solution | 100 μl of C solution |
| 11 | 100 μl of A solution | 100 μl of IV solution | 100 μl of D solution |
| 12 | 100 μl of A solution | 100 μl of IV solution | 100 μl of E solution |
| 13 | 100 μl of A solution | 100 μl of IV solution | 100 μl of F solution |
| 14 | 100 μl of A solution | 100 μl of IV solution | 100 μl of G solution |

The Results of the Mass Spectrometric Measurements:

The new compounds except decorporol came with the front in the HPLC chromatogram ($t_0$=0.5-0.6 minutes, no retention), but this fact did not affect the results of mass spectrometric tests. A minimal retention time of 0.75 minutes was registered in case of the tests with Decorporol. We registered the free complex-forming compound (M+H+DA), the calcium adduct (M−H$^+$+38 Da) and the strontium complex (M−H$^+$+86 Da) in every case. Due to the very similar chemical properties of the Ca ion and the strontium ion it is presumable that they behave similarly during ionization, therefore we have determined the selectivity compared to Ca ion by the ratio of the average mass spectrometry signals of Ca adducts to Sr adducts. In case of the measurements of the physiologically important and toxic metal ions the compound of formula (P-3) was used. The signal of the corresponding metal ion adduct was always well separated from the signal of the mother compound and from the signal of the Ca-adduct.

Using Decorporol (XI) and adducts thereof we have detected significant decarboxylation (M−45+H$^+$) products and in some cases we detected double decarboxylated derivatives (M−90+H$^+$), too. This process is well-known and leads to slow degradation of decorporol. The mono-decarboxylated and the double-decarboxylated derivatives are the main contaminants of decorporol and their solubility is very low in water, therefore beyond a certain concentration the complexes could precipitate.

The compounds of the present invention bind strontium ion stronger than decorporol. The strongest was the compound of the formula (P-3), the weakest was the compound of formula (P-1). The compound of formula (P-3) does not bind the essential ions of Zn and Fe, and binds Cu ion a little stronger than Ca ion. The compound of the formula (P-3) binds the observed toxic metal ions of Sn and Pb very strongly. It is a very important result, because the new compounds can excrete the toxic metal ions from the body very effectively, meanwhile they do not excrete the physiologically important ions. The effect of decorporol was similar, with two exceptions. Good binding was found only in the case of Zn ion, which is a result of the similar structure to EDTA. Decorporol binds Cu ion a bit stronger than the compound of the formula of (P-3), but this difference is not significant. However, it should be noted that in case of Pb ion there is a very strong decarboxylation process. In the mass spectrometry tests not only the sign of the mono-decarboxylated derivative, but the sign of double-decarboxylated derivative were higher than the signal of the decorporol-Pb complex. Probably, it is the result of the Lewis acid effect of Pb ion and therefore it can lead to a significant decomposition under physiological conditions, too.

TABLE X

Sr ion-binding ability of the complex-forming compounds (P-1), (P-2), (P-3) and Decorporol.

| compounds | $Sr^{2+}/Ca^{2+}$ rate |
|---|---|
| (P-1) | 1.25 |
| (P-2) | 1.4 |
| (P-3) | 1.5 |
| Decorporol | 1.2 |

TABLE X

Ion-binding ability of the compound (P-3) and Decorporol.

| | (P-3) compound $M^{2+}/Ca^{2+}$ rate | Decorporol $M^{2+}/Ca^{2+}$ rate |
|---|---|---|
| Sr | 1.5 | 1.2 |
| Cu | 1.1 | 1.2(+1.5) |
| Zn | ca. 0 | 8(+4)* |
| Fe | — | — |
| Sn | 100 | 22 |
| Pd | 29 | 20(+29 + 40)* |

*The peaks of decarboxylated fragments are in the brackets.

Summarized:
1. The complex-forming compounds of the formula (P-1), (P-2) and (P-3) bind Sr ion stronger than Ca ion.
2. The complex forming-compounds of the formula (P-2) and (P-3) bind the Sr ion stronger than Decorporol.
3. The MS signals of the free complex forming compounds of (P-1), (P-2) and (P-3) were significantly lower than the signals of the corresponding Sr complexes. The ratio was worse in case of decorporol, which indicates its worse complex-forming ability.
4. The decarboxylation of decorporol, which happens even in normal circumstances, worsens its complex-forming ability. A similar decarboxylation process is impossible in case of the complex-forming compounds of the formula (P-1), (P-2) and (P-3) due to their chemical structure.
5. The complex-forming compound of (P-3) binds the examined toxic metals ($Sr^{2+}$, $Sn^{2+}$, $Pd^{2+}$), then the physiological important metals ($Zn^{2+}$, $Fe^{2+}$, $Ca^{2+}$). Decorporol has a similar behavior except it binds the essential metal ion of Zn stronger than Ca, which can be dangerous.
6. The complex-forming compound of the formula (P-3) slightly binds $Cu^{2+}$ ion, better than the Ca ion, which probably does not jeopardize the Cu ion depot in the body, but the compound of the formula (P-3) can be suitable for the excretion of the superfluous amount of Cu ion in case of poisoning.
7. The metabolic properties of the complex-forming compounds of (P-1), (P-2) and (P-3) are much better, because in case of the partial or full cleavage of the side chain results in such amino acids which are already present in the body.
8. Due to the polar functional groups the solubility of the complex-forming compounds of formula (P-1), (P-2) and (P-3) is better than the solubility of decorporol.

The invention claimed is:

1. A compound of formula (I)

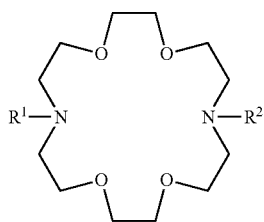

(I)

wherein $R^1$ and $R^2$ are identical or different groups of the following formula (II)

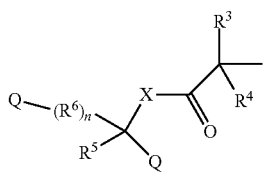

(II)

or a salt or metal ion complex thereof,
wherein
n stands for 0, 1 or 2,
Q stands for a carboxyl group,
X stands for an oxygen, sulfur or nitrogen atom,
in which the substituent of the nitrogen is a hydrogen atom or a straight or branched $C_{1-6}$ carbon chain alkyl group;

$R^3$, $R^4$ and $R^5$ are identical groups or different from each other and stand for a hydrogen atom, halogen atom, or a straight or branched $C_{1-6}$ carbon chain alkyl group, $C_{1-6}$ alkylene group, $C_{1-6}$ alkynyl group, aryl, aralkyl or heteroaryl group, saturated or unsaturated cycloalkyl group or a substituted or unsubstituted heterocyclic group containing one or more sulfur, oxygen or nitrogen atoms, which are optionally substituted with one or more identical or different substituents;

or $R^5$ and one valency of the adjacent carbon atom of $R^6$ form a double bond together according to formula (II-A)

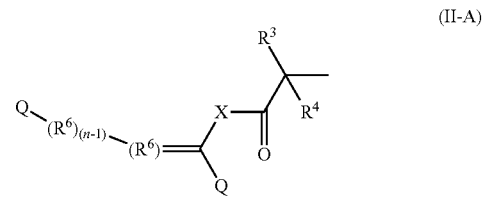

(II-A)

where n in formula (II-A) is 1 or 2;
$R^6$ stands for a saturated or unsaturated $C_1$-$C_2$ alkyl group, which is optionally substituted with one or more identical or different halogen atoms or straight or branched $C_{1-6}$ alkyl group, $C_{1-6}$ alkylene group, $C_{1-6}$ alkynyl group or aryl group, aralkyl group, heteroaryl group, or a saturated or unsaturated heterocyclic group containing one or more sulfur, oxygen or nitrogen atoms, which substituents optionally contain one or more identical or different further substituents, or $R^6$ is a group of the following formula

(III)

wherein the two carbon atoms form with the group $R^7$ a substituted or unsubstituted 3-7 membered, saturated or unsaturated ring,
or $R^5$ and $R^6$ form a substituted or unsubstituted 3-7 membered ring.

2. The compound of formula (I) according to claim 1 or a salt or metal ion complex thereof, wherein
X stands for an oxygen atom or an unsubstituted or a substituted nitrogen atom, in which the substituent of the nitrogen atom is a hydrogen atom or a methyl group.

3. The compound of formula (I) according to claim 1, or a salt or metal ion complex thereof, wherein
X stands for an oxygen atom or a substituted nitrogen atom, in which the substituent of the nitrogen atom is a hydrogen atom or a methyl group,
$R^3$, $R^4$, $R^5$ are identical or different groups which stand for a hydrogen atom, halogen atom, straight or branched $C_{1-6}$ alkyl group, aryl or aralkyl group,
$R^6$ stands for a substituted or unsubstituted methylene group, which can contain one or more identical or different substituents, which are a halogen atom, straight or branched $C_{1-6}$ alkyl group, $C_{1-6}$ alkylene group, $C_{1-6}$ alkynyl group, aryl group, aralkyl group, heteroaryl group, saturated or unsaturated cycloalkyl group, a substituted or unsubstituted heterocyclic group containing one or more sulfur, oxygen or nitrogen atoms, and optionally R⁵ and one substituent of R⁶ form an unsubstituted or substituted 3-7 membered ring.

4. The compound of formula (I) according to claim 1, or a salt or metal ion complex thereof, wherein R¹ and R² are identical and in which n stands for 0, 1 or 2 in formula (II), Q stands for a carboxyl group, X stands for a nitrogen atom in which the substituent of the nitrogen atom is a hydrogen atom or a methyl group, R³, R⁴, R⁵ are identical or different groups and are hydrogen atom, halogen atom, straight or branched carbon chain $C_{1-6}$ alkyl group, aryl or aralkyl group, R⁶ stands for an unsubstituted or substituted methylene group, which can contain one or more identical or different substituents, which are a halogen atom or a straight or branched $C_{1-6}$ alkyl group, $C_{1-6}$ alkylene group, $C_{1-6}$ alkynyl group, aryl group, aralkyl group, heteroaryl group, saturated or unsaturated cycloalkyl group, substituted or unsubstituted heterocyclic group containing one or more sulfur, oxygen or nitrogen atoms and optionally R⁵ and one of the substituents of R⁶ group form together a substituted or unsubstituted 3-7 membered ring.

5. The compound of formula (I) according to claim 4, wherein

R⁶ stands for an unsubstituted or substituted methylene group, which substituents can be identical or different, and are a straight or branched carbon chain $C_{1-6}$ alkyl group, $C_{1-6}$ alkylene group, $C_{1-6}$ alkynyl group, or a salt or metal ion complex thereof.

6. A metal ion complex according to claim 1 with one or more magnesium ions, calcium ions, strontium ions, mercury ions, tin ions or lead ions, or an alkali-metal salt.

7. A metal ion complex according to claim 1 with an alkaline earth metal salt.

8. A compound, which is one of the following compounds 2-(2-{16-[(Dicarboxymethyl-carbamoyl)-methyl]-1,4,10,13-tetraoxa-7,16-diaza-cyclooctadec-7-yl}-acetylamino)-malonic acid of formula (P-1):

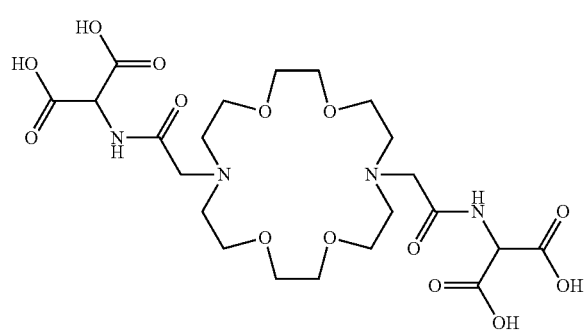

2-(2-{16-[(1,2-Dicarboxy-ethylcarbamoyl)-methyl]-1,4,10,13-tetraoxa-7,16-diaza-cyclooctadec-7-yl}-acetylamino)-succinic acid of formula (P-2):

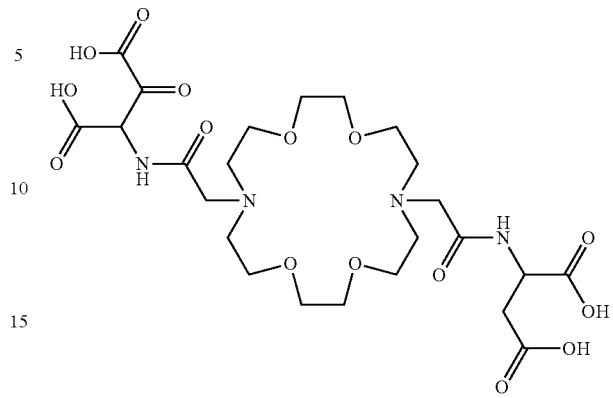

2-(2-{16-[(1,3-Dicarboxy-propylcarbamoyl)-methyl]-1,4,10,13-tetraoxa-7,16-diaza-cyclooctadec-7-yl}-acetylamino)-glutaric acid of formula (P-3):

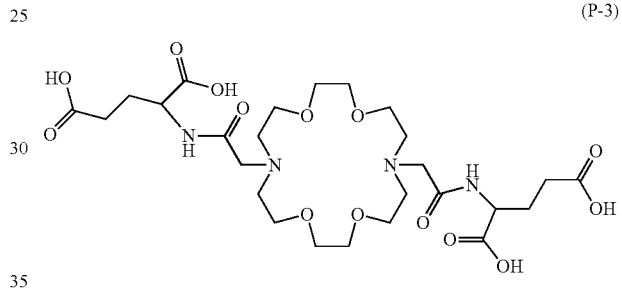

or a salt or metal ion complex thereof.

9. An acid addition salt of a compound of claim 1, containing an organic acid.

10. The compound of formula (VII)

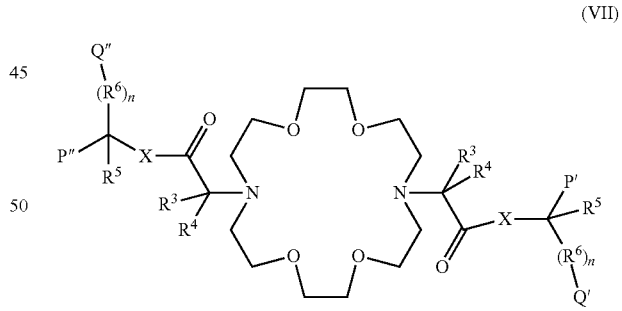

wherein n stands for 0, 1 or 2,

X stands for an oxygen, sulfur or nitrogen atom, in which the substituent of the nitrogen is a hydrogen atom or a straight or branched $C_{1-6}$ carbon chain alkyl group;

R³, R⁴ and R⁵ are identical groups or different from each other and stand for a hydrogen atom, halogen atom, or a straight or branched $C_{1-6}$ carbon chain alkyl group, $C_{1-6}$ alkylene group, $C_{1-6}$ alkynyl group, aryl, aralkyl or heteroaryl group, saturated or unsaturated cycloalkyl group or a substituted or unsubstituted heterocyclic group containing one or more sulfur, oxygen or nitrogen atoms, which are optionally substituted with one or more identical or different substituents;

or $R^5$ and one valency of the adjacent carbon atom of $R^6$ form a double bond together according to formula (II-A)

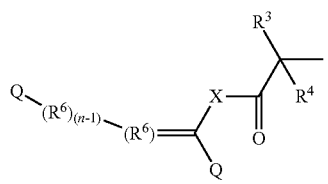

(II-A)

where n in formula (II-A) is 1 or 2;

$R^6$ stands for a saturated or unsaturated $C_1$-$C_2$ alkyl group, which is optionally substituted with one or more identical or different halogen atoms or straight or branched $C_{1-6}$ alkyl group, $C_{1-6}$ alkylene group, $C_{1-6}$ alkynyl group or aryl group, aralkyl group, heteroaryl group, or a saturated or unsaturated heterocyclic group containing one or more sulfur, oxygen or nitrogen atoms, which substituents optionally contain one or more identical or different further substituents, or $R^6$ is a group of the following formula

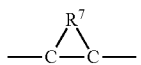

(III)

wherein the two carbon atoms form with the group $R^7$ a substituted or unsubstituted 3-7 membered, saturated or unsaturated ring, and Q',Q", P' and P''' are identical or different protected carboxyl groups or a salt or metal ion complex thereof.

11. The compound of formula (I) according to claim 1 or a salt or metal ion complex thereof, wherein $R^3$, $R^4$ and $R^5$ are identical groups or different from each other and stand for a hydrogen atom, halogen atom, or a straight or branched $C_{1-6}$ carbon chain alkyl group, $C_{1-6}$ alkylene group, $C_{1-6}$ alkynyl group, aryl, aralkyl or heteroaryl group, saturated or unsaturated cycloalkyl group or a substituted or unsubstituted heterocyclic group containing one or more sulfur, oxygen or nitrogen atoms, which are optionally substituted with one or more identical or different substituents, which are $C_{1-6}$ alkyl group, a halogen atom, a straight or branched $C_{1-6}$ carbon chain alkyl group, $C_{1-6}$ alkylene group, $C_{1-6}$ alkynyl group, aryl, aralkyl or heteroaryl group, saturated or unsaturated cycloalkyl group, or a substituted or unsubstituted heterocyclic group containing one or more sulfur, oxygen or nitrogen atoms, hydroxyl group, alkoxy group, amino group carboxyl group, alcoxycarbonyl group or carbamoyl group;

or $R^5$ and one valency of the adjacent carbon atom of $R^6$ form a double bond together according to formula (II-A)

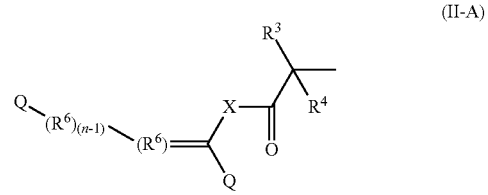

(II-A)

where n in formula (II-A) is 1 or 2;

$R^6$ stands for a saturated or unsaturated $C_1$-$C_2$ alkyl group, which is optionally substituted with one or more identical or different halogen atoms or straight or branched $C_{1-6}$ alkyl group, $C_{1-6}$ alkylene group, $C_{1-6}$ alkynyl group or aryl group, aralkyl group, heteroaryl group, or a saturated or unsaturated heterocyclic group containing one on or more sulfur, oxygen or nitrogen atoms, which substituents optionally contain one or more identical or different further substituents, which are a halogen atom, straight or branched $C_{1-6}$ alkyl, $C_{1-6}$ alkylene group, $C_{1-6}$ alkynyl group or aryl group, aralkyl group, heteroaryl group, saturated or unsaturated cycloalkyl group or a substituted or unsubstituted heterocyclic group containing on or more sulfur, oxygen or nitrogen atoms, hydroxyl group, alkoxy group, amino group, carboxyl group, alkoxycarbonyl group or carbamoyl group, or $R^6$ is a saturated or unsaturated cycloalkyl group, or an isolated or condensed, saturated or unsaturated 3-7 membered heterocyclic group containing one or more heteroatoms of sulfur, oxygen or nitrogen atoms, or an isolated or condensed aryl group, or a heteroaryl group containing one or more heteroatoms, any of which is optionally substituted with one or more identical or different substituents selected from the group consisting of a halogen atom, hydroxyl group, amino group, carboxyl group, alkoxycarbonyl group and carbamoyl group;

or $R^5$ and $R^6$ form a substituted or unsubstituted saturated or unsaturated cycloalkyl group, or an isolated or condensed heterocyclic group containing one or more heteroatoms, which cyclic group is optionally substituted with a halogen atom, hydroxyl group, $C_{1-6}$ alkyl group, $C_{1-6}$ alkylene or $C_{1-6}$ alkynyl group, alkoxy group, amino group, carboxyl group, alkoxycarbonyl group or carbamoyl group.

12. A metal ion complex according to claim 8 with one or more magnesium ions, calcium ions, strontium ions, mercury ions, tin ions or lead ions, or an alkali-metal salt.

13. An acid addition salt of a compound of claim 1, containing an acid forming compound selected from the group consisting of formic acid, acetic acid, propionic acid, butyric acid, isobutyric acid, stearic acid, decanoic acid, sebacic acid, orotic acid, palmitic acid, pamoic acid, chloroacetic acid, dichloroacetic acid, trifluoroacetic acid, 2-oxo-glutaric acid, pyruvic acid, oxalic acid, adipic acid, succinic acid, fumaric acid, maleic acid, malonic acid, benzoic acid, salicylic acid, acetyl salicylic acid, 4-aminosalicylic acid, methane sulfonic acid, ethane sulfonic acid, hydroxy-ethanesulfonic acid, cyclohexyl-sulfonic acid, dodecylsulphonic acid, ethane-1,2-disulfonic acid, p-toluenesulfonic acid, naphthalenesulfonic acid, naphthalene-2-sulfonic acid, naphthalene-1,5-disulfonic acid, glucoheptonic acid, D-gluconic acid, D-glukuronic acid, ascorbic acid, (+)-L-lactic acid, (±)-DL-lactic acid, malic acid and L-aspartic acid.

14. A metal ion complex according to claim 8 with an alkaline earth metal salt.

15. A pharmaceutical composition, comprising a compound of formula (I) of claim 1 or a salt or metal ion complex thereof and one or more pharmaceutically acceptable carriers.

16. The pharmaceutical composition according to claim 15, comprising 2-(2-{16-[(Dicarboxymethyl-carbamoyl)-methyl]-1,4,10,13-tetraoxa-7,16-diaza-cyclooctadec-7-yl}-acetylamino)-malonic acid, 2-(2-{16-[(1,2-Dicarboxy-ethyl-carbamoyl)-methyl]-1,4,10,13-tetraoxa-7,16-diaza-cyclooctadec-7-yl}-acetylamino)-succinic acid, or 2-(2-{16-[(1,3-Dicarboxy-propylcarbamoyl)-methyl]-1,4,10,13-tetraoxa-7,16-diaza-cyclooctadec-7-yl}-acetylamino)-glutaric acid or a pharmaceutically acceptable salt or metal ion complex thereof as active ingredient.

17. A method for treating heavy metal poisoning, comprising administering to a subject in need thereof an effective amount of a compound of claim 1.

18. The method according to claim 17, which treats heavy metal poisoning and associated symptoms thereof in a person or animal.

19. A method for treating heavy metal poisoning, comprising administering to a subject in need thereof an effective amount of a compound of claim 8.

20. A method for treating strontium, lead, or mercury poisoning, comprising administering to a subject in need thereof an effective amount of a compound of claim 1.

21. A method for treating strontium, lead, or mercury poisoning, comprising administering to a subject in need thereof an effective amount of a compound of claim 8.

22. A process for preparing a compound of formula (I) according to claim 1, comprising a) reacting a compound of formula (X)

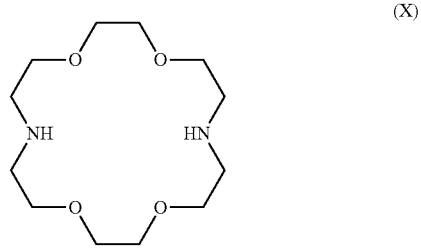 [SMILES: C1COCCOCCNCCOCCOCCN1]

(X)

with a compound of formula (II/A)

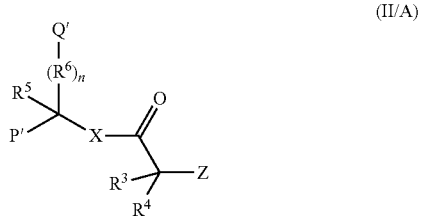

(II/A)

wherein Q' and P' stand for carboxyl groups, and Z is a leaving group, or b) forming free carboxyl groups of P', P''', Q' and Q'' in the compound of formula (VII) by removing carboxyl protecting groups

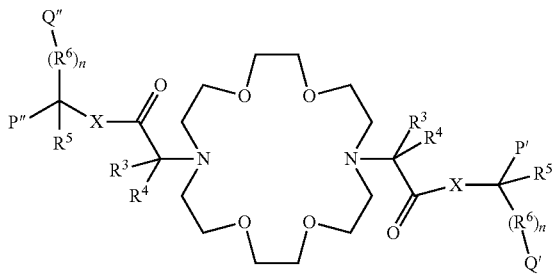

(VII)

wherein in formula (VII) P', P''', Q' and Q'' stand for identical or different protected carboxyl groups, or c) reacting a compound of formula (VI)

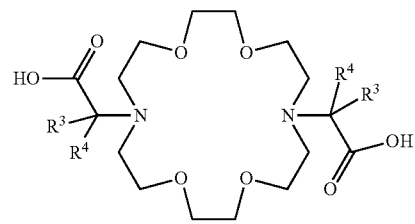

(VI)

with a compound of formula (IX)

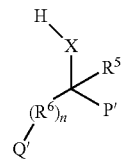

(IX)

wherein Q' and P' stand for carboxyl groups, or d) reacting the compound of formula (VI)

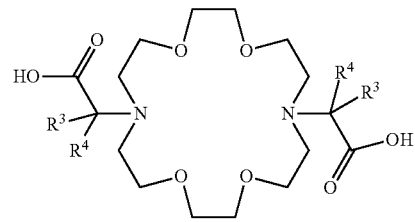

(VI)

with a compound of formula (IX)

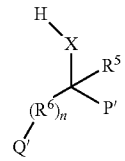

(IX)

wherein P' and Q' stand for identical or different protected carboxyl groups, and then optionally transforming the compound of formula (I) obtained in a), b), c) or d) into a salt or metal ion complex.

23. The process according to claim 22, wherein the carboxyl groups of the compound of formula (II/A) are protected and the protecting groups are removed after the reaction.

24. The process according to claim 22, wherein an organic or inorganic base is added to the reaction mixture.

25. A process for preparing a compound of formula (I) according to claim 1, comprising a)

reacting a compound of formula (I')

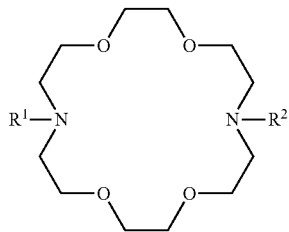

(I')

wherein $R^1$ and $R^2$ are hydrogen atoms with 1.5-2.5 mol equivalent of a compound of formula (II/A)

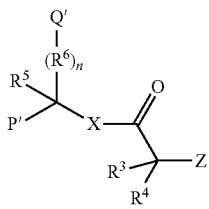

(II/A)

wherein Z stands for a leaving group, or b)

reacting a compound of formula (I')

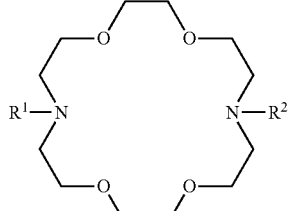

(I')

wherein $R^1$ and $R^2$ are hydrogen atoms with 0.5-1.5 mol equivalent of a first compound of the formula (II/A),

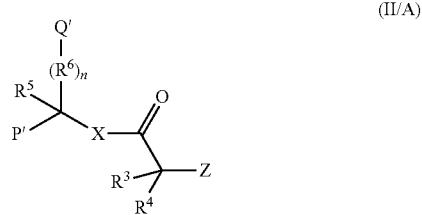

(II/A)

wherein Z stands for a leaving group, then reacting the obtained product with a second compound of formula (II/A), differing from the first compound of formula (II/A) then separating the compound of formula (I) from the reaction mixture, and optionally transforming the compound to a salt or metal ion complex.

26. A process for preparing a compound of formula (I) according to claim 1, comprising a) reacting a compound of formula (X)

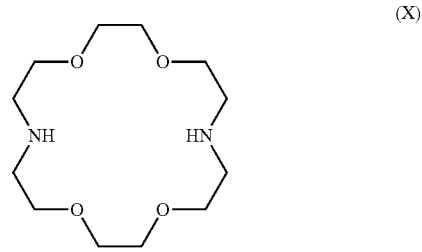 [SMILES: C1COCCOCCNCCOCCOCCN1]

(X)

with a compound of formula (II/A)

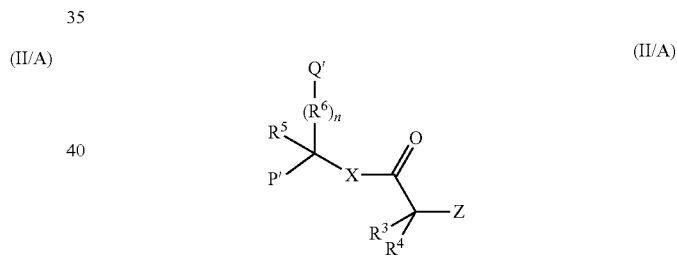

(II/A)

wherein the meaning of $R^3$, $R^4$, $R^6$, n and X corresponds to the substituents of formula (II), Q' and P' stand for carboxyl group, and Z is a leaving group selected from the group consisting of halogen atoms and aromatic or aliphatic sulfonyl-oxy groups, which are selected from the group consisting of tosiloxy, benzenesulfonyloxy and mesyloxy groups, or b) forming free carboxyl groups of P', P''', Q' and Q'' in the compound of formula (VII)

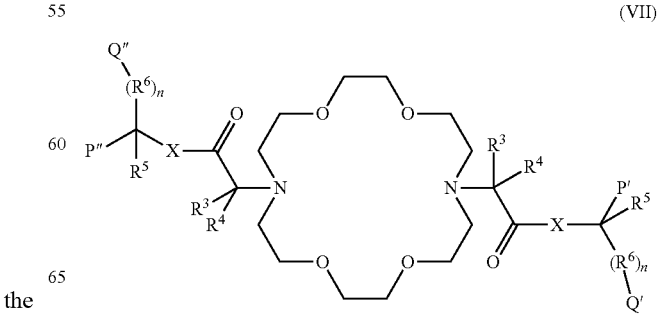

(VII)

by removing carboxyl protecting groups
wherein P', P'', Q' and Q'' stand for identical or different protected carboxyl groups selected from the group consisting of ester, amide and cyano groups or
c) reacting a compound of formula (VI)

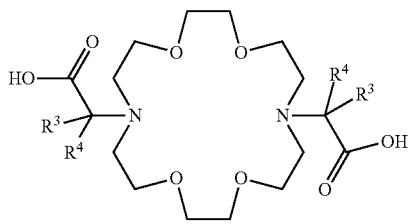
(VI)

with a compound of formula (IX)

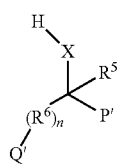
(IX)

wherein Q' and P' stand for carboxyl group,
or
d) reacting the compound of formula (VI)

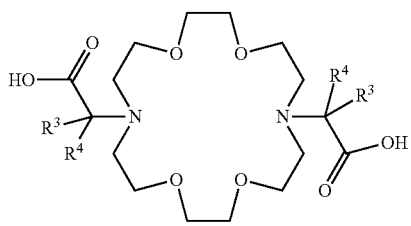
(VI)

with a compound of formula (IX)

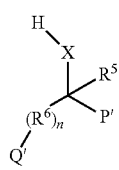
(IX)

wherein P' and Q' stand for identical or different protected carboxyl groups selected from the group consisting of ester, amide and cyano groups,
and then optionally transforming the compound of formula (I) obtained in a), b), c) or d) into a salt or metal ion complex.

27. The process according to claim 26, wherein potassium carbonate, sodium carbonate or triethylamine is added to the reaction mixture.

28. A process for preparing a compound of formula (I) according to claim 1, comprising
a) reacting a compound of formula (I')

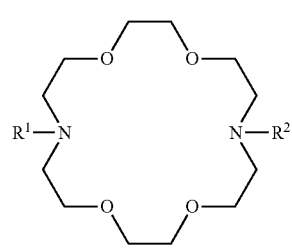
(I')

wherein $R^1$ and $R^2$ are hydrogen atoms
with 1.5-2.5 mol equivalent of a compound of formula (II/A)

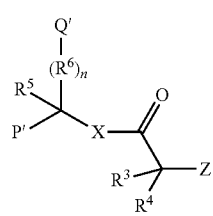
(II/A)

wherein Z stands for a leaving group selected from the group consisting of chloro, bromo, iodo atom, and an activated ester selected from the group consisting of sulfonyloxy, mesyloxy, tosyloxy and benzenesulfonyloxy groups,
or
b) reacting a compound of formula (I')

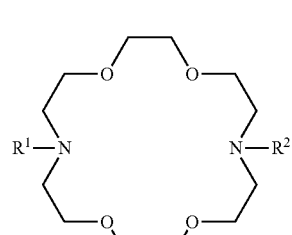
(I')

wherein $R^1$ and $R^2$ are hydrogen atoms
with 0.5-1.5 mol equivalent of a first compound of the formula (WA),

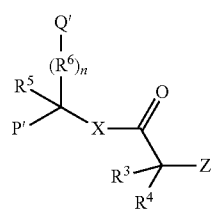
(II/A)

wherein Z stands for a leaving group selected from the group consisting of chloro, bromo, iodo atom and an activated ester selected from the group consisting of sulfonyloxy group, mesyl-, tosyl- and benzenesulfonyloxy groups, then reacting the obtained product with a second compound of formula (II/A), differing from the first compound of formula (II/A) then separating the compound of formula (I) from the reaction mixture, and optionally transforming the compound to a salt or metal ion complex.

29. A process for preparing a pharmaceutical composition according to claim 15, comprising mixing together the compound of formula (I) or a pharmaceutically acceptable salt or metal ion complex thereof with the carriers thereby providing a galenic form.

30. A process for preparing a pharmaceutical composition according to claim 16, comprising mixing together 2-(2-{16-[(Dicarboxymethyl-carbamoyl)-methyl]-1,4,10,13-tetraoxa-7,16-diaza-cyclooctadec-7-yl}-acetylamino)-malonic acid, 2-(2-{16-[(1,2-Dicarboxy-ethylcarbamoyl)-methyl]-1,4,10,13-tetraoxa-7,16-diaza-cyclooctadec-7-yl}-acetylamino)-succinic acid, or 2-(2-{16-[(1,3-Dicarboxy-propylcarbamoyl)-methyl]-1,4,10,13-tetraoxa-cyclooctadec-7-yl}-acetylamino)-glutaric acid or a pharmaceutically acceptable salt or metal ion complex thereof with the carriers thereby providing a galenic form.

* * * * *